United States Patent [19]

Heeres et al.

[11] Patent Number: 4,533,550

[45] Date of Patent: Aug. 6, 1985

[54] HETEROCYCLIC DERIVATIVES OF (4-ARYLOXYMETHYL-1,3-DIOXOLAN-2-YL)METHYL-1H-IMIDAZOLES AND 1H-1,2,4-TRIAZOLES

[75] Inventors: Jan Heeres, Vosselaar; Joseph H. Mostmans, Antwerp, both of Belgium

[73] Assignee: Janssen Pharmaceutica, N.V., Beerse, Belgium

[21] Appl. No.: 558,331

[22] Filed: Aug. 27, 1981

Related U.S. Application Data

[60] Division of Ser. No. 134,384, Mar. 27, 1980, Pat. No. 4,313,953, which is a division of Ser. No. 20,287, Mar. 14, 1979, Pat. No. 4,218,458, which is a continuation-in-part of Ser. No. 918,257, Jun. 23, 1978, abandoned.

[51] Int. Cl.$^3$ ............... C07D 239/24; A61K 31/505
[52] U.S. Cl. ................... 514/256; 544/318; 544/333; 544/331; 514/269; 514/275
[58] Field of Search ............ 424/269; 544/333, 318, 544/331; 548/143

[56] References Cited

U.S. PATENT DOCUMENTS 4,218,458  8/1980  Heenes et al. ............ 424/269
4,313,953  2/1982  Heenes et al. ............ 424/269

Primary Examiner—Nicholas S. Rizzo
Attorney, Agent, or Firm—Geoffrey G. Dellenbaugh

[57] ABSTRACT

Novel heterocyclic derivatives of (4-aryloxymethyl-1,3-dioxolan-2-yl)methyl-1H-imidazoles and 1H-1,2,4-triazoles, useful as antifungal and antibacterial agents.

4 Claims, No Drawings

HETEROCYCLIC DERIVATIVES OF (4-ARYLOXYMETHYL-1,3-DIOXOLAN-2-YL)METHYL-1H-IMIDAZOLES AND 1H-1,2,4-TRIAZOLES

CROSS-REFERENCE TO RELATED APPLICATIONS

This is a division of application Ser. No. 134,384, filed Mar. 27, 1980, now U.S. Pat. No. 4,313,953, which in turn is a division of application Ser. No. 20,287, filed Mar. 14, 1979 now U.S. Pat. No. 4,218,458, which in turn is a continuation-in-part of application Ser. No. 918,257, filed June 23, 1978, now abandoned.

BACKGROUND OF THE INVENTION

In U.S. Pat. No. 3,936,470 and Belg. Pat. No. 837,831 there are described a number of 1-(1,3-dioxolan-2-ylmethyl)-1H imidazoles and 1H-1,2,4-triazoles having antifungal and anti-bacterial properties. The compounds of this invention differ from the foregoing essentially by the substitution of the aryloxy moiety with a heterocyclic group, the latter being attached to said aryloxy group by a carbon-carbon bond. Similar compounds wherein a heterocyclic radical is attached to the aryloxy group by a carbon-nitrogen bond are described in U.S. pat. appln. Ser. No. 853,726, filed Nov. 21, 1977.

DESCRIPTION OF THE PREFERRED EMBODIMENTS

This invention is concerned with novel 1H-imidazole and 1H-1,2,4-triazole derivatives which may structurally be represented by the formula:

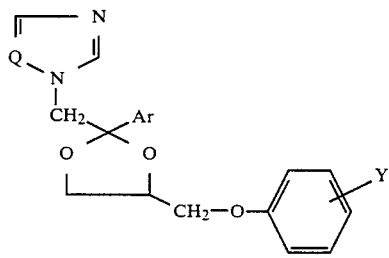

and the pharmaceutically acceptable acid addition salts and stereochemically isomeric forms thereof, wherein:

Q is a member selected from the group consisting of CH and N;

Ar is a member selected from the group consisting of thienyl, halothienyl, phenyl and substituted phenyl, said substituted phenyl having from 1 to 3 substituents each independently selected from the group consisting of halo, lower alkyl and lower alkyloxy; and the radical Y is a member selected from the group consisting of a pyrimidin-4-yl radical of the formula

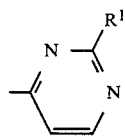 (a)

wherein $R^1$ is a member selected from the group consisting of hydrogen, lower alkyl, lower alkenyl, lower alkynyl, lower alkyloxy, lower alkenyloxy, lower alkynyloxy, lower alkyloxy-lower alkyloxy, aryllower alkyloxy, lower alkylthio, aryllower alkylthio, hydroxy, mercapto, amino, mono- and di- lower alkylamino, cycloalkylamino, lower alkylcarbonylamino, arylcarbonylamino, arylamino, aryl lower alkyl amino and aryl:

a heterocyclic radical of the formula

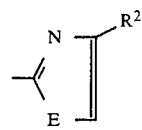 (b)

wherein $R^2$ is selected from the group consisting of hydrogen, lower alkyl and aryllower alkyl and E is a member selected from the group consisting of $NR^3$, O and S, wherein said $R^3$ is selected from the group consisting of hydrogen, lower alkyl and aryllower alkyl;

a heterocyclic radical of the formula

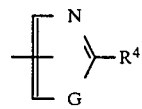 (c)

wherein $R^4$ is selected from the group consisting of hydrogen, lower alkylthio, aryllower alkylthio, lower alkyl and aryllower alkyl and G is a member selected from the group consisting of $NR^5$, O and S, wherein said $R^5$ is selected from the group consisting of hydrogen, lower alkyl and aryllower alkyl, provided that said G is $NR^5$ when said $R^4$ stands for alkylthio;

a heterocyclic radical of formula

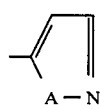 (d)

wherein A is selected from the group consisting of O and $NR^6$, said $R^6$ being selected from the group consisting of hydrogen, lower alkyl, hydroxylower alkyl, aryl and aryllower alkyl;

a heterocyclic radical of formula

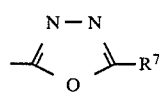 (e)

wherein $R^7$ is selected from the group consisting of hydrogen and lower alkyl;

wherein said aryl as used in the foregoing definitions is selected from the group consisting of phenyl and substituted phenyl, said substituted phenyl having from 1 to 3 substituents each independently selected from the group consisting of halo, lower alkyl, lower alkyloxy and trifluoromethyl.

It is understood that radicals of formula (a) wherein $R^1$ stands for hydroxy or mercapto may also exist under their tautomeric oxo, respectively thioxo, forms. Such oxo and thioxo forms, although not explicitly indicated in the above structures, are naturally intended to be within the scope of formula (I).

The preferred compounds of this invention are those where the radical Y is attached to the phenoxymethyl moiety in the para position.

As used in the foregoing and in following definitions, the term "halo" is generic to fluoro, chloro, bromo and iodo; "lower alkyl" is meant to include straight and branched hydrocarbon radicals having from 1 to 6 carbon atoms such as, for example, methyl, ethyl, 1-methylethyl, 1,1-dimethylethyl, propyl, 1-methylpropyl, 2-methylpropyl, butyl, pentyl, hexyl and the like; "lower alkenyl" and "lower alkynyl" are meant to include straight and branched alkenyl, respectively alkynyl, radicals having from 3 to 6 carbon atoms, wherein the unsaturation is preferably located at the β-position, but can also be located at the γ, δ or ε-positions, such as, for example, 2-propenyl, 2-butenyl, 3-methyl-2-butenyl and the like, and, respectively 2-propynyl, 2-butynyl, 4-methyl-2-pentynyl and the like; and the term "cycloalkyl" designates cyclopropyl, cyclobutyl, cyclopentyl and cyclohexyl.

In order to simplify the structural representation of compounds (I) and of certain starting materials and intermediates used in the preparation thereof, the 2-Ar-2-(1H-imidazol-1-ylmethyl or 1H-1,2,4-triazol-1-ylmethyl)-1,3-dioxolan-4-yl group, wherein Ar is as previously defined, will hereafter be represented by the formula D:

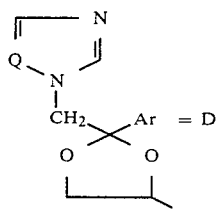

Q = CH or N

The compounds of formula (I) wherein Y is as previously defined, but other then a radical of formula (a) wherein $R^1$ is hydroxy or mercapto, said Y being represented by $Y^1$ and said compounds by the formula (I-a), can generally be prepared by the reaction of an appropriate reactive ester of the formula (II) with an appropriately substituted phenol of formula (III).

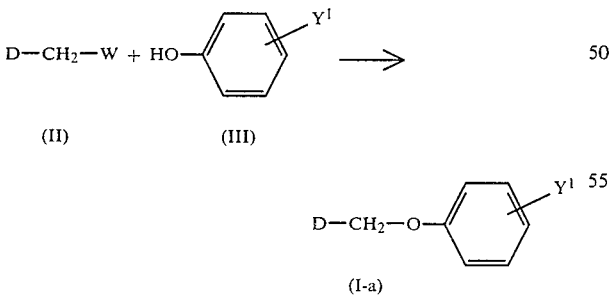

In formula (II), W has the meaning of a reactive ester residue such as, for example, halo, preferably chloro, bromo or iodo, or a sulfonyloxy group such as, for example, methylsulfonyloxy, 4-methylphenylsulfonyloxy and the like.

The reaction of (II) with (III) is carried out under art-known conditions of performing O-alkylations with reactive esters. The reaction is generally carried out in an appropriate reaction-inert organic solvent such as, for example, N,N-dimethylformamide, N,N-dimethylacetamide, hexamethylphosphoric triamide, dimethylsulfoxide, 4-methyl-2-pentanone and the like, optionally in admixture with other reaction inert solvents such as, for example, aromatic hydrocarbons, e.g., benzene, methylbenzene, dimethylbenzene and the like. Further it is advantageous to add to the reaction mixture an appropriate base such as, for example, an alkali metal hydride or carbonate, in order to enhance the rate of the reaction. Otherwise it may be advantageous to first convert the substituted phenol (III) into a metal salt thereof, preferably the sodium salt, in the usual manner, e.g., by the reaction of (III) with metal bases such as sodium hydride, sodium hydroxide and the like, and to use thereafter said metal salt in the reaction with (II). Somewhat elevated temperatures are appropriate to enhance the reaction rate and most preferably the reaction is carried out at from about 80° C. to about 130° C.

Compounds of formula (I) wherein Y has the formula (a) or (d), said Y being represented by $Y^2$ and said compounds by the formula (I-b), can also be prepared by cyclizing an appropriate intermediate (IV) with an appropriate cyclizing agent and, if desired, introducing suitable substituents into the thus obtained heterocyclic compounds.

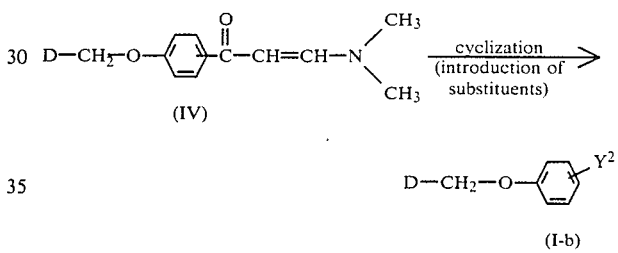

The nature of the cyclizing agents to be used depends upon the nature of $Y^2$ in the desired compounds (I-b) as will be explained hereafter.

Compounds of formula (I-b) wherein $Y^2$ has the formula (a) wherein $R^1$ is hydrogen, lower alkyl, lower alkenyl, lower alkynyl, aryl, amino, mono- and di-lower alkyl amino, aryllower alkylamino, cycloalkylamino or arylamino, said $R^1$ being represented by $R_a^1$ and said compounds by the formula (I-b-1) can conveniently be prepared by cyclizing the intermediate of formula (IV) with an appropriate imidamide of formula (V), wherein $R_a^1$ has the above indicated meaning.

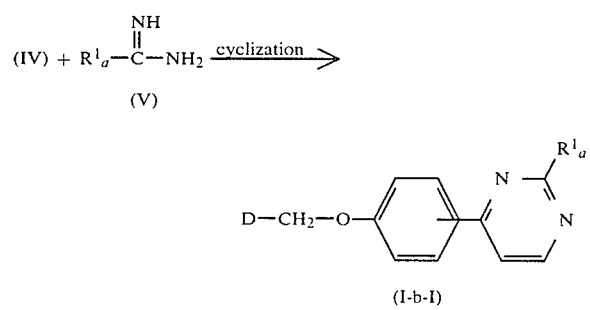

The reaction is conveniently carried out by mixing and melting the reactants together, preferably while heating under I.R.-irradiation, if desired in the presence of a reaction-inert organic solvent, having a relatively high boiling point, e.g., 1,1'-oxybis(2-methoxyethane), and preferably in the presence of a base such as, for example, sodium acetate or an alkali alkanolate, most preferably in the presence of the corresponding alcohol.

The compounds of formula (I-b) wherein $Y^2$ has the formula (a) wherein $R^1$ stands for hydroxy or mercapto, said $R^1$ being represented by XH, wherein X is O or S, and said compounds being represented by the formula (I-b-2), can be prepared by cyclizing the intermediate of formula (IV) with urea (VI-a), respectively thiourea (VI-b).

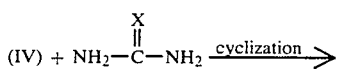

(VI-a) X = O
(VI-b) X = S

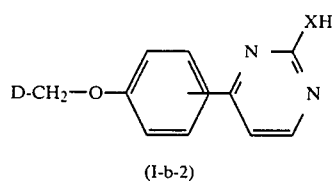

(I-b-2)

The reaction is carried out following the same reaction conditions as previously described for the preparation of compounds of formula (I-b-1) starting from (IV) and (V).

Compounds of formula (I-b) wherein $Y^2$ has the formula (d) wherein A stands for O, said compounds being represented by (I-b-3), may be prepared by cyclizing the intermediate of formula (IV) with hydroxylamine by stirring the reactants together during several days in the presence of a suitable reaction-inert organic solvent such as, for example, a lower alcohol, e.g., methanol or ethanol; an amide, e.g., N,N-dimethylformamide, hexamethylphosphoric triamide; dimethylsulfoxide; 4-methyl-2-pentanone; and the like, preferably at an elevated temperature and most preferably at the reflux temperature of the reaction mixture in order to enhance the rate of the reaction

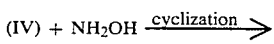

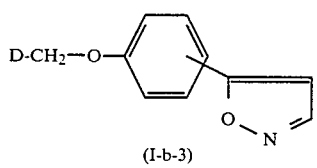

(I-b-3)

Compounds of formula (I-b) wherein $Y^2$ has the formula (d) wherein A stands for $NR^6$ and wherein $R^6$ has the previously defined meaning, said compounds being represented by (I-b-4), can easily be prepared by cyclizing the intermediate of formula (IV) with an appropriate hydrazine of formula (VII).

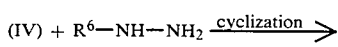

(VII)

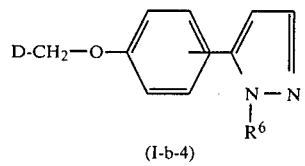

(I-b-4)

The reaction is carried out following the same reaction conditions as previously described for the preparation of compounds of formula (I-b-3), starting from (IV) and hydroxylamine.

Compounds of formula (I-b) wherein $Y^2$ has the formula (a) wherein $R^1$ is an acylamino radical of the formula $NH-CO-R^8$, wherein $R^8$ stands for lower alkyl or aryl, said compounds being represented by the formula (I-b-5), can be prepared by N-acylating a compound of formula (I-b-1) wherein $R_a^1$ is amino, said compounds being represented by (I-b-1'), with an appropriate arylcarbonyl halogenide or lower alkylcarbonyl halogenide of the formula $R^8$-CO-halo, wherein halo is preferably chloro or bromo.

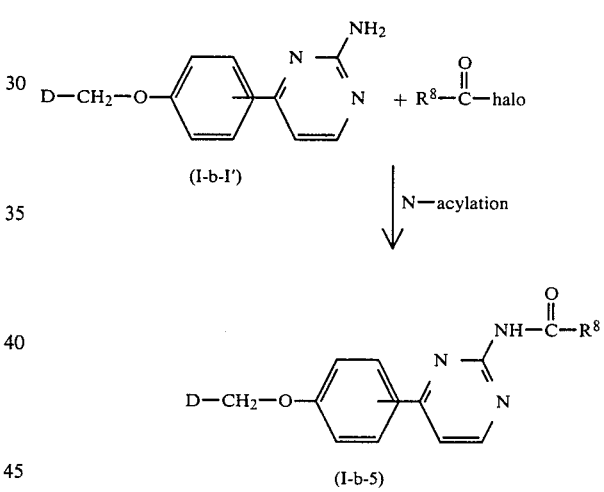

The reaction is conveniently carried out in the presence of a relatively polar organic solvent such as, for example, pyridine or 2,4,6-trimethylpyridine, preferably in the presence of a catalyst, e.g., N,N-dimethylpyridinamine, and most preferably at an elevated temperature in order to enhance the rate of the reaction.

The compounds of formula (I-b) wherein $Y^2$ has the formula (a) wherein $R^1$ stands for lower alkylthio, aryllower alkylthio, lower alkyloxy, lower alkenyloxy, lower alkynyloxy, aryllower alkyloxy and lower alkyloxy-lower alkyloxy, said $R^1$ being represented by $R^9X$, wherein X is O or S and $R^9$ stands for lower alkyl, aryl lower alkyl, lower alkenyl, lower alkynyl or lower alkyloxy-lower alkyl, and said compounds being represented by the formula (I-b-6), can easily be prepared by S-alkylating, respectively O-alkylating, a compound of formula (I-b-2) with di (lower alkyl)sulfate or with an appropriate reactive ester of the formula (VIII), wherein W is as previously defined.

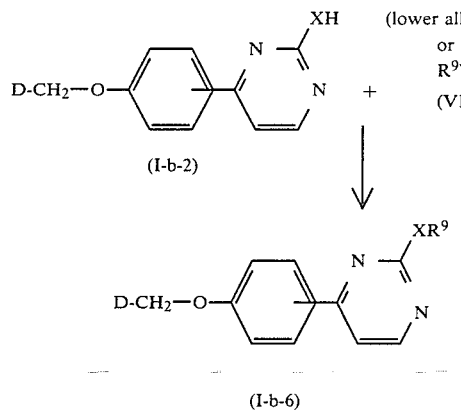

(I-b-2) → (I-b-6)

The reaction is carried out following art-known conditions of performing O- and S-alkylations with reactive esters as previously defined.

The compounds of formula (I-b) wherein $Y^2$ has the formula (c) wherein $R^4$ stands for hydrogen and G is O, said compounds being represented by the formula (I-b-7) can be prepared by the cyclization of an aldehyde of formula (IX) with 1-[(isocyanatomethyl)sulfonyl]-4-methylbenzene (X), following the same procedure as described in Tetrahedron Letters, 2369 (1972).

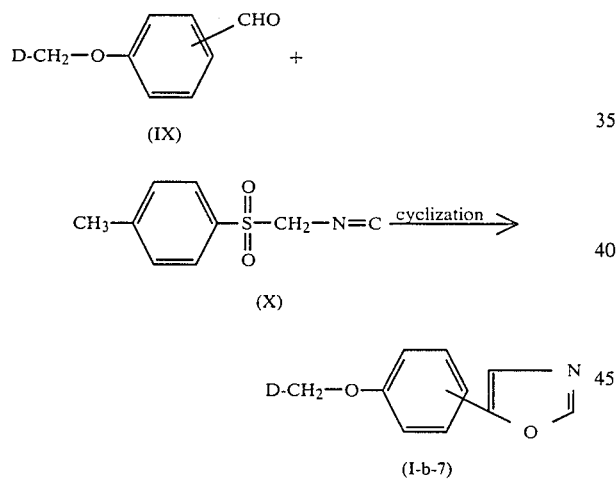

The imidazole and triazole derivatives of formula (I), obtained in base form in the foregoing preparations, may be converted to their therapeutically useful acid addition salts by reaction with an appropriate acid, as, for example, an inorganic acid such as hydrohalic acid, i.e., hydrochloric, hydrobromic or hydroiodic acid; sulfuric, nitric or thiocyanic acid; a phosphoric acid; an organic acid such as acetic, propanoic, hydroxyacetic, 2-hydroxypropanoic, 2-oxopropanoic, ethanedioic, propanedioic, 1,4-butanedioic, (Z)-2-butenedioic, (E)-2-butenedioic, 2-hydroxy-1,4-butanedioic, 2,3-dihydroxy-1, 4-butanedioic, 2-hydroxy-1,2,3-propanetricarboxylic, benzoic, 3-phenyl-2-propenoic, α-hydroxybenzeneacetic, methanesulfonic, ethanesulfonic, 2-hydroxyethanesulfonic, 4-methylbenzensulfonic, 2-hydroxybenzoic, 4-amino-2- hydroxybenzoic, 2-phenoxybenzoic or 2-acetyloxybenzoic acid. The salts are in turn converted to the corresponding free bases in the usual manner, e.g., by reaction with alkali such as sodium or potassium hydroxide.

A number of the intermediates and starting materials used in the foregoing preparations are known compounds, others may be prepared according to art-known methodologies of preparing similar compounds and some of them are novel and consequently their preparation will be described hereafter.

The intermediates of formula (III) are generally known and they may all be prepared following methods described in the literature for preparing such known or similar compounds, such as, for example, the following.

The intermediates of formula (III) wherein $Y^1$ has the formula (c) wherein $R^4$ stands for lower alkylthio or aryllower alkylthio and G is $NR^5$, said $R^5$ being as previously defined, and wherein the aryloxy group is attached to the 5-position of the heterocyclic group, said compounds being represented by the formula (III-a), can be prepared by first reacting 2-(methoxyphenyl)-1,3-dioxolane-2-methanamine (XI) with an appropriate isothiocyanatoalkane of formula (XII), subsequently reacting the thiourea derivative (XIII) with a reactive ester of formula (XIV), wherein W is as previously defined and $R^{10}$ stands for lower alkyl or aryllower alkyl, cyclizing the thus obtained S-(lower alkyl)-isothiourea derivative (XV) and hydrolyzing the methoxy-function of the thus obtained compounds of formula (XVI). The foregoing reactions are illustrated as follows:

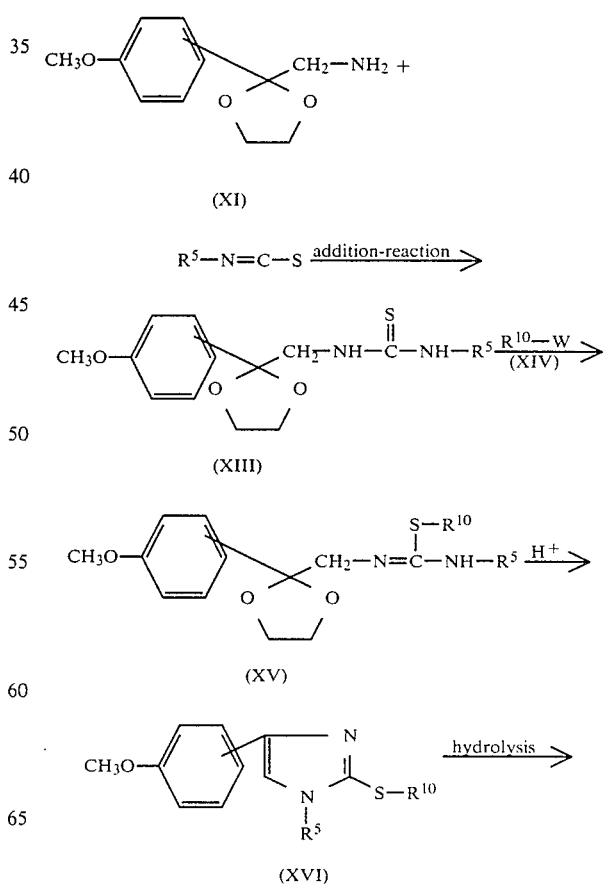

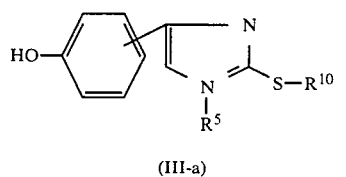

(III-a)

The addition-reaction of (XI) with (XII) to produce a thiourea of formula (XIII) is carried out by stirring and heating the reactants together in a reaction-inert solvent such as, for example, a lower alcohol, preferably in the presence of an appropriate base such as, for example, a metal carbonate, e.g., potassium carbonate. The reaction of (XIII) with (XIV) is carried out following standard S-alkylating procedures, e.g., by stirring and heating the reactants together in an appropriate reaction-inert organic solvent such as a lower alcohol. The cyclization of (XV) is carried out in acid medium such as, for example, aqueous hydrochloric acid, at an elevated temperature during several hours. The hydrolysis of the methoxy-group of compound (XVI) is carried out by refluxing (XVI) for several hours in hydrobromic acid in glacial acetic acid.

2-(Methoxyphenyl)-1,3-dioxolane-2-methanamine (XI) may be prepared by ketalizing 2-]2-(methoxyphenyl)-2-oxoethyl]-1H-isoindole-1,3-(2H)-dione, (XVII), with ethanediol according to the procedures outlined in Synthesis, 1974 (I), 23 and thereafter subjecting the thus obtained dioxolane of formula (XVIII) to alkaline hydrolysis to liberate the primary amino group. The foregoing reactions are illustrated as follows.

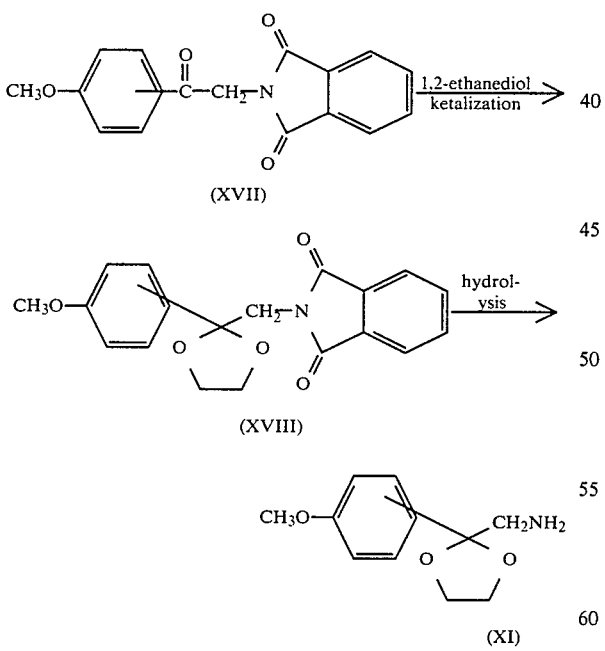

The intermediates of formula (III) wherein $Y^1$ has the formula (c) wherein $R^4$ stands for lower alkylthio or aryllower alkythio and G is $NR^5$, said $R^5$ being as previously defined, and wherein the aryloxy group is attached to the heterocyclic group at the 4-position of this heterocyclyl, said compounds being represented by the formula (III-b) can be prepared by carrying out the steps of:

(i) cyclizing an appropriate 2-amino-1-(hydroxyphenyl)ethanone derivative of formula (XIX) with an appropriate alkali metal thiocyanate, preferably potassium thiocyanate;

(ii) S-alkylating the thus obtained (XX) with an appropriate reactive ester (XIV) wherein W and $R^{10}$ are as previously defined, or with an appropriate di(lower alkyl)sulfate, following art-known procedures whereupon 0-alkylation simultaneously occurs; and (iii) subjecting the thus obtained intermediate of formula (XXI) to acid hydrolysis to liberate the phenolic hydroxyl group from the corresponding lower alkylether.

The foregoing reactions are illustrated as follows:

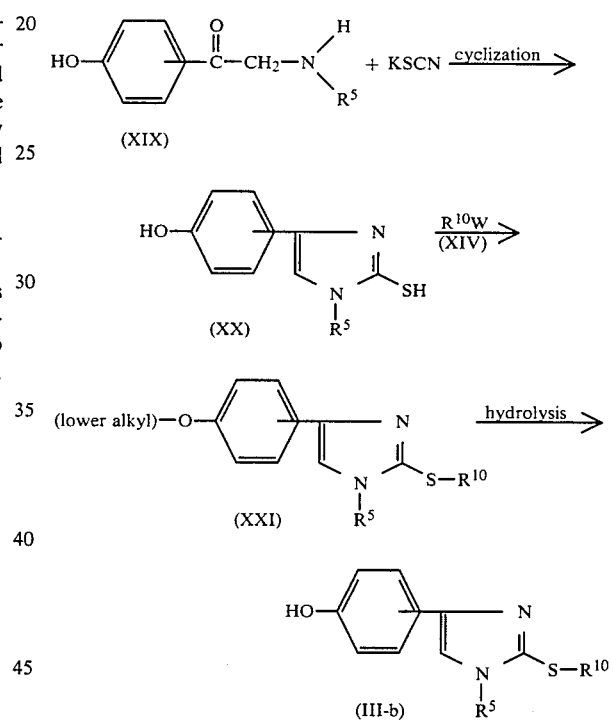

The cyclization-reaction is carried out by stirring the reactants together for several hours in a suitable polar solvent such as, for example, water, preferably in admixture with a water-miscible reaction-inert solvent such as, for example, 1,4-dioxane and the like or a lower alcohol, e.g., ethanol, most preferably at an elevated temperature in order to enhance the rate of the reaction. The S-alkylation reaction is carried out following standard S-alkylation methods and the hydrolysis of the lower alkylether is carried out following the previously described method for the hydrolysis of (XVI).

The intermediates of formula (III) wherein $Y^1$ has the formula (c) wherein $R^4$ stands for hydrogen and G is $NR^5$, said $R^5$ being as previously defined and wherein the aryloxy group is attached to the 4 position of the heterocyclic group, said compounds being represented by the formula (III-b'), can be prepared by desulfurating either a compound of formula (XX) or a compound of formula (III-b).

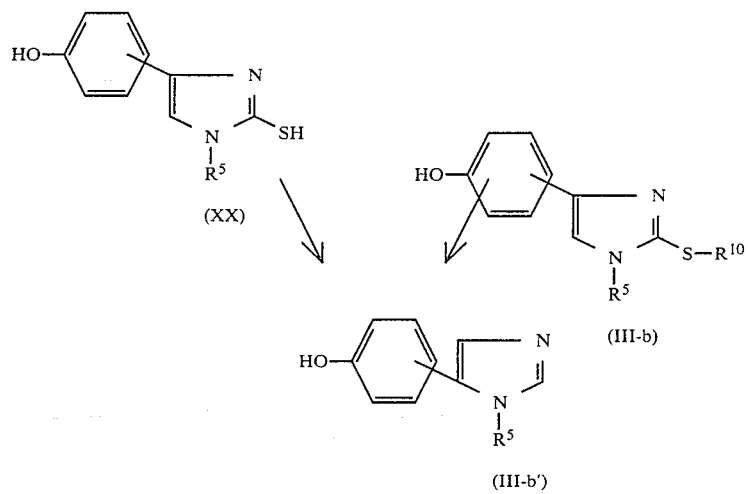

The desulfuration is carried out by art-known procedures, e.g., by stirring and heating the compounds of formula (XX) or (III-b) for several hours with Raney-nickel in an appropriate reaction-inert organic solvent such as, for example, a lower alcohol, e.g., ethanol and the like, preferably in the presence of a base, such as, for example, ammonia. In certain circumstances it may be appropriate to simultaneously introduce hydrogen into the reaction mixture. It is understood that said desulfurations may also be carried out using instead of a phenol a corresponding lower alkylether as a starting material and afterwards cleaving the ether group by acid hydrolysis as previously described herein.

The intermediates of formula (III) wherein $Y^1$ has the formula (c) wherein $R^4$ stands for hydrogen and G is $NR^5$, said $R^5$ being as previously defined and wherein the aryloxy-group is attached to the 5-position of the heterocyclic ring, said compounds being represented by the formula (III-a'), can be prepared by N-alkylating a compound of formula (III-b') wherein $R^5$ stands for phenylmethyl, said compounds being represented by the formula (III-b'-1), with an appropriate reactive ester $R^5$-W, wherein $R^5$ and W are as previously defined, following standard N-alkylating procedures to obtain a quaternary imidazolium salt of formula (XXII) and subsequently removing the phenylmethyl group of the latter in the usual manner, e.g., by catalytic hydrogenation in the presence of an appropriate catalyst such as, for example, palladium-on-charcoal.

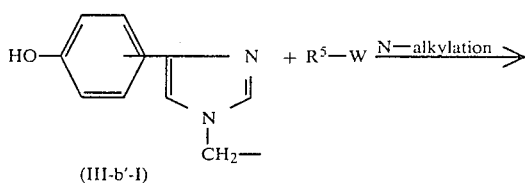

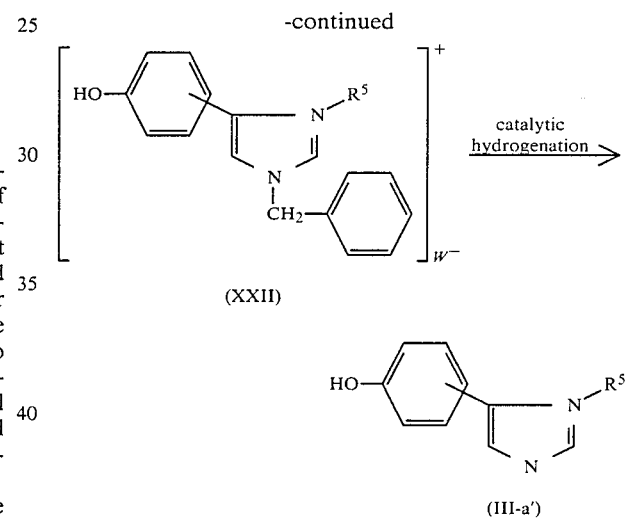

The intermediates of formula (III-a') can alternatively be prepared by desulfurating a compound of formula (III-a) following procedures similar to those described herein for the desulfuration of (XX) or (III-b).

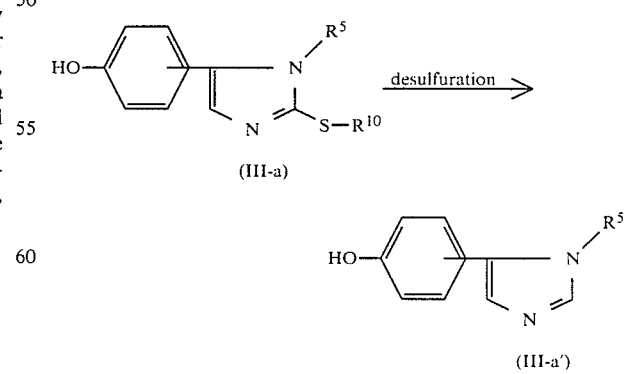

The intermediates of formula (III), wherein $Y^1$ has the formula (b) wherein $R^2$ and E are as previously defined, said compounds being represented by the formula (III-c), can be prepared by cyclizing a compound of formula (XXIII) in acid medium.

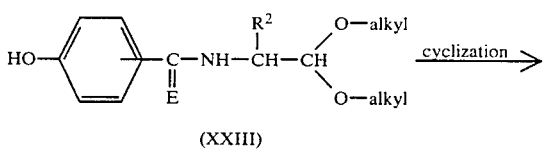

(XXIII)

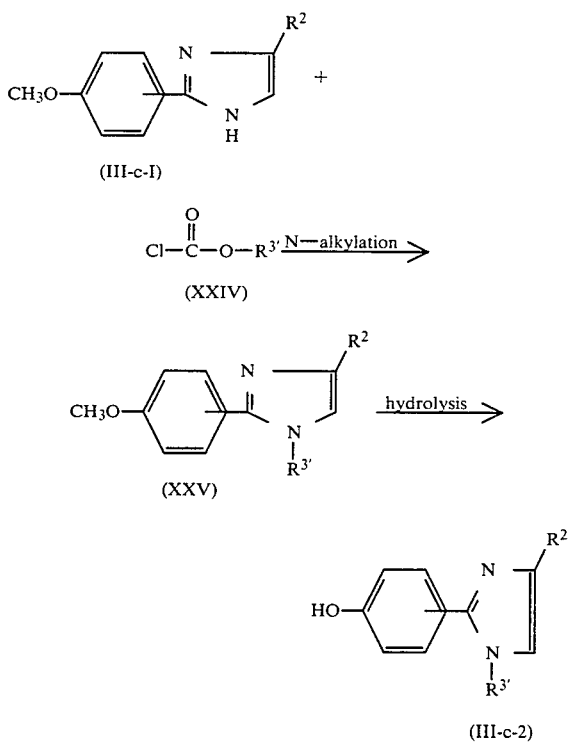

The compounds of formula (III-c) wherein $R^2$ is as previously defined and E is $Nr^3$, wherein $R^3$ stands for lower alkyl or aryllower alkyl, said $R^3$ being represented by $R^{3'}$ and said compounds by the formula (III-c-2), can easily be prepared by N-alkylating a compound of formula (III-c) wherein E is NH, and wherein $R^2$ is as previously defined, said compounds being represented by the formula (III-c-1), with an appropriate carbonochloridate of the formula (XXIV), wherein $R^3$ is lower alkyl or aryllower alkyl, in the presence of a suitable base such as for example, N,N-diethylethanamide, and in the presence of an appropriate reaction-inert solvent such as, for example, a hydrocarbon, e.g., benzone, n.hexane and the like; or a nitrile, e.g., acetonitrile, propionitrile and the like, and subsequently hydrolyzing the methoxy-group of the thus obtained (XXV) in the previously described manner.

The intermediates of formula (III) wherein $Y^1$ has the formula (c) wherein $R^4$ is as previously defined and G stands for S can generally be prepared following the procedures described in J. Am. Chem. Soc. 68, 871 (1946) and 67, 2242 (1945) and Helv. 44, 1429 (1961).

The compounds of formula (III) wherein $Y^1$ has the formula (e) wherein $R^7$ is as previously defined, said compounds being represented by the formula (III-d) can be prepared by the reaction of a hydroxybenzoic acid hydrazide of formula (XXV) with a tri(alkoxy)-alkane of formula Z(XXVI). The reaction is carried out by stirring and heating the reactants together for several hours.

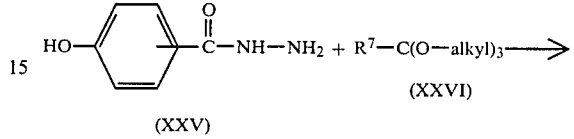

(XXV) (XXVI)

(III-d)

Intermediates of formula (II) wherein Q stands for CH and methods of preparing the same are described in Belg. Pat. No. 837,831. In general the reactive esters of formula (II) can be prepared along the following sequence of reactions.

An appropriate 1-Ar-2-bromoethanone of formula (XXVII) is subjected to a ketalization reaction with 1,2,3-propanetriol following methodologies analogous to those described in Synthesis 1974 (I), 23. In a preferred manner of carrying out the reaction both reactants are refluxed together for several hours with azeotropic water removal in an appropriate organic solvent, preferably in the presence of a simple alcohol, such as, for example, ethanol, propanol, butanol, pentanol and the like, and in the presence of an appropriate strong acid such as 4-methylbenzenesulfonic acid. Suitable organic solvents are, for example, aromatic hydrocarbons, such as benzene, methylbenzene, dimethylbenzene and the like and saturated hydrocarbons, such as cyclohexane.

The thus obtained dioxolane (XXVIII) is then reacted with benzoyl chloride to obtain a benzoate of the formula (XXIX) and the latter is subsequently reacted with 1H-imidazole or 1H-1,2,4-triazole. Said reaction is preferably carried out by stirring and heating the reactants together in a suitable organic solvent, e.g., N,N-dimethylformamide, in the presence of an appropriate strong metal base, e.g., sodium methanolate, to obtain an intermediate of the formula (XXX). The desired reactive esters of formula (II) are then conviently prepared by first hydrolyzing (XXX) in alkaline medium and thereafter converting the hydroxy group of the thus obtained (XXXI) into a reactive ester thereof according to methodologies generally known in the art. For example, methanesulfonates and 4-methylbenzenesulfonattes are conveniently prepared by the reaction of the alcohol with methanesulfonyl chloride or 4-methylbenzenesulfonyl chloride and halides may be prepared by the reaction of the alcohol with an appropriate halogenating agent such as, for example, thionyl chloride, phosphor pentachloride, phosphor pentabromide, phosphoryl chloride and the like. When the reactive ester is an iodide, it is preferably derived from the corresponding chloride or bromide by the replacement of that halogen with iodine.

The foregoing reactions may be illustrated as follows:

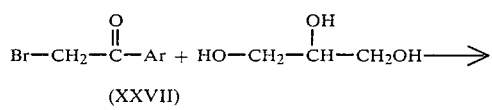

(XXVII)

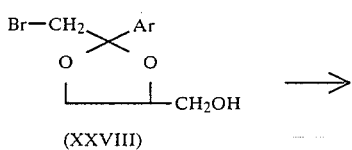

(XXVIII)

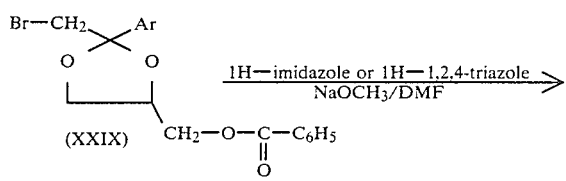

(XXX)

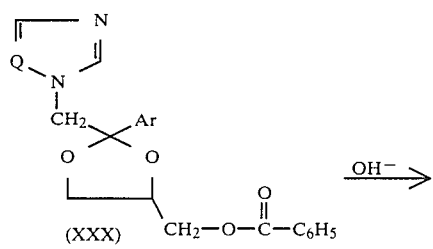

(XXXI)  CH₂OH

| reactive ester formation
↓
(II)

The intermediates of formula (IV) can be prepared by the reaction of a compound of formula (XXXII) with 1,1-dimethoxy-N,N-dimethylmethanamine. Said reaction is preferably carried out by stirring and heating the reactants together in the presence of a suitable organic solvent, e.g., N,N-dimethylformamide.

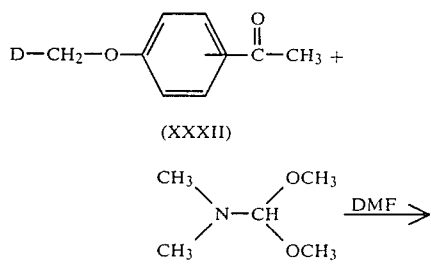

(XXXII)

CH₃    OCH₃
  \\N—CH   DMF →
CH₃    OCH₃

-continued

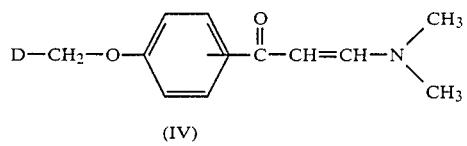

(IV)

The starting materials of formula (XXXII) can be prepared by O-alkylating an appropriately substituted phenol of formula (XXXII) with a reactive ester of formula (II), wherein W has the previously defined meaning, following the same procedure as described herein for the preparation of (I-a) starting from (II) and (III).

D—CH₂—W +

(II)

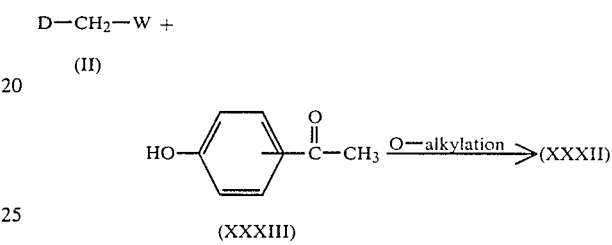

(XXXIII)

The ultimate starting materials in all of the foregoing preparations are generally known and they may all be prepared following methods described in the literature for the preparation of such known or similar compounds.

From formula (I) it is evident that the compounds of this invention have at least two asymmetric carbon atoms in their structures, namely those located in the 2- and 4-position of the dioxolane nucleus, and consequently they can exist under different stereochemically isomeric forms. The stereochemically isomeric forms of (I) and the pharmaceutically acceptable acid addition salts thereof are intended to be within the scope of this invention.

The diastereomeric racemates of (I), denoted as cis and trans forms respectively, according to the rules described in C.A., 76, Index Guide, Section IV, p. 85 (1972), may be obtained separately by conventional methods. Appropriate methods which may advantageously be employed therefore include, for example, selective crystallization and chromatographic separation, e.g. column-chromatography.

Since the stereochemical configuration is already fixed in the intermediates (II) and (IV) it is also possible to separate cis and trans forms at this or even an earlier stage, whereupon the corresponding forms of (I) may be derived therefrom in the previously indicated manner. The separation of cis and trans forms of such intermediates may be performed by conventional methods as described hereabove for the separation of cis and trans forms of the compounds (I).

It is evident that the cis and trans diastereomeric racemates may be further resolved into their optical isomers, cis(+), cis(−), trans(+) and trans(−) by the application of methodologies known to those skilled in the art.

The compounds of formula (I) and the pharmaceutically acceptable acid addition salts thereof are useful agents in combatting fungi and bacteria. For example, said compounds and acid addition salts thereof were found to be highly active against a wide variety of fungi such as, for example, *Microsporum canis, Ctenomyces mentagrophytes, Trichophyton rubrum, Phialophora verrucosa, Cryptococcus neoformans, Candida tropicalis, Candida albicans,* Mucor species, *Aspergillus fumigatus, Sporotricum schenckii* and Saprolegnia species, and against bacteria such as, for example, *Erysipelotrix insidiosa,* Staphylococci such as *Staphylococcus hemolyticus* and Streptococci such as *Streptococcus pyogenes.* In view of their potent, local as well as systemic, antimicrobial activity the compounds of this invention constitute useful tools for the destruction or prevention of the growth of fungi and bacteria and more particularly they can effectively be used in the treatment of subjects suffering from such microorganism.

The strong antimicrobial activity of the compounds (I) is clearly evidenced by the data obtained in the following experiments, which data is only given to illustrate the useful antimicrobial properties of all the compounds (I) and not to limit the invention either with respect to the scope of susceptible microorganisms nor with respect to the scope of formula (I).

EXPERIMENT A

Activity of compounds (I) against vaginal candidosis in rats

Female Wistar rats of ±100 g body weight are used. They are ovariectomized and hysterectomized and after three weeks of recovery, 100 μg of oestradiol undecylate in sesame oil is given subcutaneously once a week for 3 consecutive weeks. The thus induced pseudooestrus is controlled by microscopic examination of vaginal smears. Food and water are left available ad libitum. The rats are infected intravaginally with $8.10^5$ cells of Candida albicans, grown on Sabouraud broth for 48 hours at 37° C. and diluted with saline. The date of infection varies from day +25 to day +32 after surgical intervention, depending on the appearance of signs of induced pseudo-oestrus.

The drugs under investigation are administered orally once a day for two days starting from the day of infection. For each experiment there are placebo treated controls. The results are assessed by taking vaginal smears with sterile swabs on several days after the infection. The swabs are put into Sabouraud broth in petri-dishes and incubated for 48 hours at 37° C. If no growth of *Candida albicans* occurs, i.e., when the animals are negative at the end of the experiment, this is due to drug administration because it never happens in placebo treated controls.

The table below gives the lowest oral dose of the drug under investigation which is found active at the 14th day after infection.

EXPERIMENT B

Activity of compounds (I) against crop candidosis in turkeys

Turkeys of 14 days old are infected in the crop with $4.10^6$ *Candida albicans* cells, grown of Sabouraud broth for 48 hours at 37° C. and diluted with saline. The volume of the inoculum is 1 ml. The drugs under investigation are premixed in 500 mg of lacton and thereafter admixed in 1000 g of meal without any additives. The concentration of the drug under investigation in the meal is expressed in mg/kg.

The animals are given the medicated feed for 13 consecutive days starting on the day of infection. At the end of the experiment all animals are sacrificed. At autopsy the crops are removed, emptied and grinded in an ultra-turrax mixer in 15 ml of sterile saline. Colony counting is done on Sabouraud agar and the results given in the table represents the $ED_{50}$, i.e., the dose of the drug whereby the crops of 50% of the animals are completely negative for *Candida albicans.*

The compounds listed in the Table are intended to illustrate and not to limit the scope of the present invention.

| Y | Q | Base or Salt | Vaginal candidosis in rats: lowest effective dose in mg/kg orally | Crop candidosis in turkeys: $ED_{50}$ in mg/kg in feed |
|---|---|---|---|---|
| pyrazine | —CH— | 2HNO₃ | 2.5 | 16 |
| 2-methylamino-pyrimidine | —CH— | base | 1.25 | 31 |
| oxazole | —CH— | base | 2.5 | <31 |

-continued

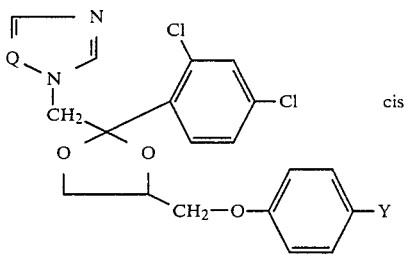
cis

| Y | Q | Base or Salt | Vaginal candidosis in rats: lowest effective dose in mg/kg orally | Crop candidosis in turkeys: $ED_{50}$ in mg/kg in feed |
|---|---|---|---|---|
| (oxadiazole) | —CH— | base | 1.25 | 16 |
| (methyloxadiazole) | —CH— | base | 2.5 | 8 |
| (n-propylimidazole) | —CH— | $2HNO_3$ | 2.5 | 31 |
| (N-methylpyrazole) | —CH— | base | 2.5 | 16 |
| (methyloxadiazole) | —N— | base | 0.63 | 16 |
| (ethyl-SCH3-imidazole) | N | $HNO_3$ | 1.25 | >31 |
| (oxadiazole) | N | base | 0.63 | >31 |
| (methyl-SCH3-imidazole) | N | $2HNO_3$ | 1.25 | 31 |

In view of their antifungal and antibacterial properties this invention provides valuable compositions comprising the subject compounds of formula (I) or acid addition salts thereof as the active ingredient in a solvent or a solid, semi-solid or liquid diluent or carrier, and, in addition, it provides an effective method of combatting fungal or bacterial growth by use of an effective antifungal or antibacterial amount of such compounds (I) or salts thereof. Antifungal and antibacterial compositions comprising an effective amount of an active compound (I), either alone or in combination with other active therapeutic ingredients, in admixture with suitable carriers may be readily prepared according to conventional pharmaceutical techniques for the usual routes of administration.

Preferred compositions are in dosage unit form, comprising per dosage unit an effective quantity of the active ingredient in admixture with suitable carriers. Although the amount of the active ingredient per unit dosage may vary within rather wide limits, dosage units comprising from about 50 to about 500 mg and more particularly from about 100 to about 250 mg of the active ingredient are preferred.

The following examples are intended to illustrate and not to limit the scope of the present invention. Unless otherwise stated all parts therein are by weight.

EXAMPLE I

A mixture of 2.6 parts of 1,1-dimethoxy-N,N-dimethylmethanamine, 9 parts of cis-1-{4-[2-(2,4-dichlorophenyl)-2-(1H-imidazol-1-ylmethyl)-1,3-dioxolan-4-ylmethoxy]phenyl}ethanone and 67.5 parts of N,N-dimethylformamide is stirred and refluxed overnight. The reaction mixture is cooled, poured onto water and the product is extracted twice with benzene. The combined extracts are dried, filtered and evaporated. The residue is crystallized from methylbenzene. The product is filtered off and dried, yielding 4.6 parts (46%) of cis-1-{4-[2-(2,4-dichlorophenyl)-2-(1H-imidazol-1-ylmethyl)-1,3-dioxolan-4-ylmethoxy]phenyl}-3-(dimethylamino)-2-propen-1-one; mp. 144.7° C.

EXAMPLE II

A mixture of 94 parts of 2-[2-(4-methoxyphenyl)-2-oxoethyl]-1H-isoindole-1,3(2H)-dione, 21 parts of 1,2-ethanediol, 3 parts of 4-methylbenzenesulfonic acid, 40 parts of 1-butanol and 450 parts of methylbenzene is stirred and refluxed for 15 hours using a water-separator. The reaction mixture is cooled and washed with a diluted sodium hydroxide solution. The organic phase is dried, filtered and evaporated. The solid residue is triturated in 2,2'-oxybispropane. The product is filtered off and dried, yielding 102 parts of 2-[2-(4-methoxyphenyl)-1,3-dioxolan-2-ylmethyl]-1H-isoindole-1,3(2H)-dione.

A mixture of 102 parts of 2-[2-(4-methoxyphenyl)-1,3-dioxolan-2-ylmethyl]-1H-isoindole-1,3(2H)-dione and 650 parts of sodium hydroxide solution 30% is stirred and refluxed for 60 hours. The reaction mixture is cooled and the product is extracted with trichloromethane. The extract is washed with water, dried filtered and evaporated. The oily residue is stirred in 2,2'-oxybispropane. The mixture is filtered and the filtrate is saturated with hydrogen chloride. The formed hydrochloride salt is filtered off and dried, yielding 35 parts of 2-(4-methoxyphenyl)-1,3-dioxolane-2-methanamine hydrochloride.

EXAMPLE III

A mixture of 22 parts of 2-(4-methoxyphenyl)-1,3-dioxolane-2-methanamine hydrochloride, 11.5 parts of 1-isothiocyanato-2-methylpropane, 20.7 parts of potassium carbonate and 200 parts of 2-propanol is stirred and refluxed for 3 hours. The reaction mixture is filtered while hot and the filtrate is evaporated. The solid residue is crystallized from a mixture of benzene and petroleumether. The product is filtered off and dried, yielding 26 parts (89.65%) of N-[2-(4-methoxyphenyl)-1,3-dioxolan-2-ylmethyl]-N'-(2-methylpropyl)thiourea; mp. 96° C.

In a similar manner are also prepared:
N-[2-(4-methoxyphenyl)-1,3-dioxolan-2-ylmethyl]-N'-(1-methylethyl)thiourea; mp. 96.2° C.;
N-butyl-N'-[2-(4-methoxyphenyl)-1,3-dioxolan-2-ylmethyl]thiourea; mp. 110.1° C.;
N-[2-(4-methoxyphenyl)-1,3-dioxolan-2-ylmethyl]-N'-propylthiourea; mp. 94.5° C.;
N-ethyl-N'-[2-(4-methoxyphenyl)-1,3-dioxolan-2-ylmethyl]thiourea; and
N-[2-(4-methoxyphenyl)-1,3-dioxolan-2-ylmethyl]-N'-methylthiourea.

EXAMPLE IV

A mixture of 5 parts of N-[2-(4-methoxyphenyl)-1,3-dioxolan-2-ylmethyl]-N'-propylthiourea, 3.5 parts of iodomethane and 60 parts of ethanol is stirred and heated for 2 hours at about 50° C. The reaction mixture is evaporated and the oily residue is crystallized from ethyl acetate. The product is filtered off and dried, yielding 5.5 parts of methyl N-[2-(4-methoxyphenyl)-1,3-dioxolan-2-ylmethyl]-N'-propylcarbamimidothioate monohydroiodide; mp. 91.2° C.

In a similar manner are also prepared:
methyl N-[2-(4-methoxyphenyl)-1,3-dioxolan-2-ylmethyl]-N'-(1-methylethyl)carbamimidothioate monohydroiodide; mp. 150.9° C.;
methyl N-butyl-N'-[2-(4-methoxyphenyl)-1,3-dioxolan-2-methyl]-carbamimidothioate monohydroiodide; mp. 103° C.;
methyl N-[2-(4-methoxyphenyl)-1,3-dioxolan-2-ylmethyl]-N'-(2-methylpropyl)carbamimidothioate; mp. 125.4° C.;
S-methyl N-ethyl-N'-[2-(4-methoxyphenyl)-1,3-dioxolan-2-ylmethyl]carbamimidothioate monohydroiodide; mp. 145.2° C.;
S-methyl N'-[2-(4-methoxyphenyl)-1,3-dioxolan-2-ylmethyl]-N-methylcarbamimidothioate monohydroiodide.

EXAMPLE V

A mixture of 7 parts of methyl N-[2-(4-methoxyphenyl)-1,3-dioxolan-2-ylmethyl]-N'-propylcarbamimidothioate monohydroiodide and 30 parts of hydrochloric acid solution 10% is stirred and refluxed for 1.50 hours. The reaction mixture is cooled and neutralized with sodium hydrogen carbonate. The product is extracted with 1,1'-oxybisethane. The extract is dried, filtered and saturated with hydrogen chloride. The precipitated oil solidifies upon scratching. The product is filtered off and crystallized from a mixture of 2-propanol and 2,2'-oxybispropane, yielding 4 parts (86%) of 5-(4-methoxyphenyl)-2-methylthio)-1-propyl-1H-imidazole monohydrochloride; mp. 149.2° C.

In a similar manner are also prepared:
5-(4-methoxyphenyl)-1-(1-methylethyl)-2-(methylthio)-1H-imidazole monohydrochloride; mp. 191.7° C.;
1-butyl-5-(4-methoxyphenyl)-2-(methylthio)-1H-imidazole monohydrochloride; mp. 123.1° C.;
5-(4-methoxyphenyl)-1-(2-methylpropyl)-2-(methylthio)-1H-imidazole monohydrochloride; mp. 168.3° C.;
5-(4-methoxyphenyl)-1-methyl-2-(methylthio)-1H-imidazole; mp. 130.4° C.; and
1-ethyl-2-(methylthio)-5-(4-methoxyphenyl)-1H-imidazole mononitrate; mp. 93.8° C.

EXAMPLE VI

A mixture of 3 parts of 5-(4-methoxyphenyl)-2-(methylthio)-1-propyl-1H-imidazole and 37.5 parts of hydrobromic acid solution 48% in glacial acetic acid is stirred and refluxed for 2.50 hours. The reaction mixture is cooled and neutralized with sodium hydrogen carbonate. The precipitated product is filtered off, washed with water and crystallized from a mixture of ethanol and water, yielding 2 parts of 4-[2-(methylthio)-1-propyl-1H-imidazol-5-yl]phenol; mp. 157.4° C.

In a similar manner are also prepared:
4-[1-(1- methylethyl)-1H-imidazol-5-yl]phenol;
4-(1-butyl-1H-imidazol-5-yl)phenol; mp. 168.4° C.; and 4-[1-(2-methylpropyl)-1H-imidazol-5-yl]phenol; mp. 187.2° C.

EXAMPLE VII

A mixture of 12 parts of 4-[2-(methylthio)-1-propyl-1H-imidazol-5-yl]phenol, 10 parts of Raney-nickel catalyst and 80 parts of ethanol is stirred and refluxed for 2 hours. The Raney-nickel is filtered off and the filtrate is stirred and refluxed for 2 hours with another 10 parts of Raney-nickel catalyst. The Raney-nickel catalyst is filtered off and the filtrate is evaporated, yielding 5.5 parts (61%) of 4-(1-propyl-1H-imidazol-5yl)phenol; mp. 160° C.

EXAMPLE VIII

A mixture of 7.5 parts of 5-(4-methoxyphenyl)-1-(1-methylethyl)-2-(methylthio)-1H-imidazole, 10 parts of Raney-nickel catalyst and 80 parts of ethanol is stirred refluxed for 2 h. The catalyst is filtered off and another 10 parts of Raney-nickel catalyst is added. The whole is stirred for 2 hours at reflux temperature. The Raney-nickel catalyst is filtered off and the filtrate is evaporated, yielding 4 parts of 5-(4-methoxyphenyl)-1-(1-methylethyl)-1H-imidazole as a solid residue.

In an analogous manner there are also prepared:
4-(1-methyl-1H-imidazol-5-yl)phenol; mp. 254.6° C.; and
4-(1-ethyl-1H-imidazol-5-yl)phenol; mp. 156.9° C.

EXAMPLE IX

A mixture of 11 parts of 1-butyl-5-(4-methoxyphenyl)-2-(methylthio)-1H-imidazole monohydrochloride, 20 parts of Raney-nickel catalyst, 105 parts of ammonium hydroxide and 8 parts of methanol is stirred for 2 hours at room temperature. The Raney-nickel catalyst is filtered off and another 20 parts of Raney-nickel catalyst is added. The whole is stirred for another 2 hours at room temperature. The catalyst is filtered off and the filtrate is evaporated. The residue is taken up in a small amount of water and the product is extracted with dichloromethane. The extract is dried, filtered and evaporated. The residue is purified by column-chromatography over silica gel using a mixture of trichloromethane and methanol (97:3 by volume) as eluent. The pure fractions are collected and the eluent is evaporated, yielding 8 of 1-butyl-5-(4-methoxyphenyl)-1H-imidazole as an oily residue.

In a similar manner there is also prepared:
5-(4-methoxyphenyl)-1-(2-methylpropyl)-1H-imidazole as an oily residue.

EXAMPLE X

To a stirred and refluxing mixture of 21.5 parts of 2-(ethylamino)-1-(4-hydroxyphenyl)ethanone hydrochloride, 60 parts of ethanol and 75 parts of water is added dropwise a solution of 12 parts of potassium thiocyanate in a small amount of water. Upon completion, stirring is continued overnight at reflux temperature. Another portion of 4 parts of potassium thiocyanate in small amount of water is added and the whole is stirred for 8 hours at reflux temperature. The reaction mixture is concentrated. The product is filtered off and crystallized from a mixture of ethanol and water, yielding 10 parts (91%) of 4-(1-ethyl-2-mercapto-1H-imidazol-4-yl)phenol; mp. 251.7° C.

In a similar manner there are als prepared:
4-(2-mercapto-1-methyl-1H-imidazol-4-yl)phenol; mp. 280° C.;
4-[2-mercapto-1-(phenylmethyl)-1H-imidazol-4-yl]phenol; mp. 238.8° C.;
4-(2-mercapto-1-propyl-1H-imidazol-4-yl)phenol; mp. 244.5° C.; and
4-[2-mercapto-1-(1-methylethyl)-1H-imidazol-4-yl]phenol; mp. 230° C.

EXAMPLE XI

To a stirred mixture of 10 parts Raney-nickel catalyst and 96 parts of ethanol are added successively 9 parts of ammonium hydroxide and 9 parts of 4-(1-ethyl-2-mercapto-1H-imidazol-4-yl)phenol. Stirring is continued for 2 hours at reflux temperature. The reaction mixture is filtered and the filtrate is evaporated. The precipitated product is filtered off, washed with a small amount of a mixture of 2,2'-oxybispropane and ethanol, and dried, yielding 6.7 parts of 4-(1-ethyl-1H-imidazol-4-yl)phenol.

In a similar manner are also prepared:
4-(1-propyl-1H-imidazol-4-yl)phenol; mp. 231.9° C.;
4-[1-(1-methylethyl)-1H-imidazol-4-yl]phenol; mp. 222.3° C.; and
4-[1-(phenylmethyl)-1H-imidazol-4-yl]phenol; mp. 224.2° C.

EXAMPLE XII

To a stirred solution of 3.25 parts of potassium hydroxide solution 86% in 80 parts of methanol are added 11 parts of 4-(1-ethyl-2-mercapto-1H-imidazol-4-yl)phenol and stirring is continued till all solid enters solution. Then there are added 6.9 parts of dimethyl sulfate and the whole is stirred overnight at room temperature. The precipitate is filtered off and the filtrate is evaporated. The solid residue is stirred with water. The product is filtered off and crystallized from 4-methyl-2-pentanone, yielding 7 parts (60%) of 4-[1-ethyl-2-(methylthio)-1H-imidazol-4-yl]phenol; mp. 218.2° C.

EXAMPLE XIII

A mixture of 10 parts of 4-(2-mercapto-1-methyl-1H-imidazol-4-yl)phenol and 50 parts of dimethyl sulfoxide is stirred at room temperature till all solid enters solution. Then there are added 3.2 parts of sodium hydride dispersion 78% and stirring is continued till gas evolution has ceased. A solution of 10.9 parts of bromoethane in a small amount of dimethyl sulfoxide is added dropwise (slowly). Upon completion, stirring is continued for 1 hour at room temperature. The reaction mixture is poured onto water. The precipitated product is filtered off and crystallized from 2,2'-oxybispropane. The product is filtered off and dried, yielding 7 parts of 4-(4-ethoxyphenyl)-2-(ethylthio)-1-methyl-1H-imidazole; mp. 98.2° C.

In a similar manner there is also prepared:
4-(4-ethoxyphenyl)-1-ethyl-2-(ethylthio)-1H-imidazole; mp. 69.8° C.

EXAMPLE XIV

A mixture of 20 parts of 4-(4-ethoxyphenyl)-2-(ethylthio)-1-methyl-1H-imidazole and 37.5 parts of hydrobromic acid solution 48% in glacial acetic acid is stirred and refluxed for 3 hours. The reaction mixture is cooled and neutralized with sodium hydrogen carbonate. The precipitated product is filtered off and crystallized from 4-methyl-2-pentanone, yielding 5 parts of 4-[2-(ethylthio)-1-methyl-1H-imidazol-4-yl]phenol; mp. 209.9° C.

In a similar manner there are also prepared:

4-[1-ethyl-2-(ethylthio)-1H-imidazol-4-yl]phenol; mp. 210°–212° C.;

4-[1-methyl-2-(methylthio)-1H-imidazol-5-yl]phenol; mp. 201.1° C.; and

4-[1-ethyl-2-(methylthio)-1H-imidazol-5-yl]phenol; mp. 212.1° C.

EXAMPLE XV

Through a stirred and refluxing mixture of 5.5 parts of 4-[1-(phenylmethyl)-1H-imidazol-4-yl]phenol and 120 parts of acetonitrile, gaseous bromomethane is bubbled till the solution is clear. Stirring at reflux is continued for 2 hours while gaseous bromomethane is still introduced. The solvent is evaporated and the solid residue is triturated in 2-propanone. The product is filtered off and dried, yielding 7.5 parts of 4-(4-hydroxyphenyl)-3-methyl-1-(phenylmethyl)-1H-imidazolium bromide.

In a similar manner there is also prepared:
3-ethyl-4-(4-hydroxyphenyl)-1-(phenylmethyl)-1H-imidazolium bromide.

EXAMPLE XVI

A mixture of 7 parts of 3-ethyl-4-(4-hydroxyphenyl)-1-(phenylmethyl)-1H-imidazolium bromide and 120 parts of ethanol is hydrogenated at normal pressure and at room temperature with 2 parts of palladium-on-charcoal catalyst 10%. After the calculated amount of hydrogen is taken up, the catalyst is filtered off and the filtrate is evaporated. The oily residue solidifies on scratching in 2-propanone. The product is filtered off and dried, yielding 5 parts of 4-(1-ethyl-1H-imidazol-5-yl)phenol monohydrobromide.

In a similar manner there is also prepared:
4-(1-methyl-1H-imidazol-5-yl)phenol; mp. 257.5° C.

EXAMPLE XVII

To a stirred and cooled (10° C.) mixture of 7 parts of 2-(4-methoxyphenyl)-1H-imidazole, 4.2 parts of N,N-diethylethanamine and 40 parts of acetonitrile is added dropwise a solution of 6.5 parts of ethyl carbonochloridate in a small amount of 1,1'-oxybisethane at a temperature below 10° C. Upon completion, stirring is continued overnight at room temperature. The reaction mixture is poured onto 175 parts of 1,1'-oxybisethane and the whole is stirred. The precipitate is filtered off and the filtrate is washed three times with water, dried, filtered and evaporated. The oily residue is heated to 180° C., cooled and dissolved in 1,1'-oxybisethane. The undissolved material is filtered off and the ether-phase is saturated with hydrogen chloride. The formed hydrochloride salt is filtered off and triturated in 2-butanone, yielding 3 parts of 1-ethyl-2-(4-methoxyphenyl)-1H-imidazole monohydrochloride.

A mixture of 7 parts of 1-ethyl-2-(4-methoxyphenyl)-1H-imidazole monohydrochloride and 75 parts of hydrobromic acid solution 48% in glacial acetic acid is stirred and a refluxed for 2 hours. The reaction mixture is concentrated and a small amount of water is added to the concentrate. The whole is neutralized with sodium hydrogen carbonate. The precipitated product is filtered off and crystallized from a mixture of ethanol and water, yielding 3.3 parts of 4-(1-ethyl-1H-imidazol-2-yl)phenol.

EXAMPLE XVIII

A mixture of 1.3 parts of 4-hydroxybenzaldehyde, 4.2 parts of cis-2-(2,4-dichlorophenyl)-2-(1H-imidazol-1yl-methyl)-1,3-dioxolan-4-ylmethyl methanesulfonate, 2 parts of potassium carbonate and 68 parts of N,N-dimethylformamide is stirred overnight at 100° C. The reaction mixture is cooled and poured onto water. The product is extracted twice with 1,1'-oxybisethane. The combined extracts are washed with water, dried, filtered and evaporated. The residue is converted into the nitrate salt in 4-methyl-2-pentanone and 2,2'-oxybispropane. The salt is filtered off and crystallized from a mixture of ethanol and 2,2'-oxybispropane yielding 4.3 parts (87%) of cis-4-[2-(2,4-dichlorophenyl)-2-(1H-imidazol-1-ylmethyl)-1,3-dioxolan-4-ylmethoxy]benzaldehyde nitrate; mp. 158.1° C.

EXAMPLE XIX

A mixture of 9.6 parts of 4-hydroxybenzoic acid hydrazide and 44 parts of 1,1', 1"-[ethylidynetris(oxy)]-trisethane is stirred and refluxed overnight. The precipitated product is filtered off and crystallized from 1-butanol, yielding 10.5 parts (99%) of 4-(5-methyl-1,3,4-oxadiazol-2-yl)phenol; mp. 238.8° C.

In a similar manner there is also prepared:
4-(1,3,4-oxadiazol-2-yl)phenol; mp. 218.2° C.

EXAMPLE XX 3.1 Parts of methanimidamide acetate and 5 parts of cis-1-{4-[2-(2,4-dichlorophenyl)-2-(1H-imidazol-1-ylmethyl)-1,3-dioxolan-4-ylmethoxy]phenyl}-3-(dimethylamino)-2-propen-1-one are heated under I.R.-radiation for one hour. The resulting melt is allowed to cool to room temperature and water is added. The product is extracted with trichloromethane. The extract is washed with water, dried, filtered and evaporated. The residue is converted into the nitrate salt in 2-propane and 2,2'-oxybispropane. The salt is filtered off and crystallized from ethanol, yielding 2.9 parts (48%) of cis-4-{4-[2-(2,4-dichlorophenyl) - 2-(1H-imidazol-1-yl-methyl)-1,3-dioxolan-4-ylmethoxy]phenyl}pyrimidine dinitrate; mp. 168.1° C.

EXAMPLE XXI

A mixture of 2 parts of ethanimidamide hydrochloride, 5 parts of cis-1-{4-[2-(2,4-dichlorophenyl)-2-(1H-imidazol-1-ylmethyl)1,3-dioxolan-4-ylmethoxy]-phenyl}-3-(dimethylamino)-2-propen-1-one and 2 parts of sodium acetate is stirred and heated under IR-radiation for one hour. The resulting melt is cooled, water is added and the product is extracted with trichloromethane. The extract is dried, filtered and evaporated. The residue is converted into the nitrate salt in 2,2'-oxybispropane. The salt is filtered off and crystallized from a mixture of ethanol and 2,2'-oxybispropane, yielding 3 parts (47% of cis-4-{4-[2-(2,4-dichlorophenyl)-2-(1H-imidazol-1-yl-methyl)-1,3-dioxolan-4-ylmethoxy]-phenyl}-2-methylpyrimidine dinitrate hemihydrate; mp. 125.7° C.

In a similar manner there are also prepared:
cis-4-{4-[2-(2,4-dichlorophenyl)-2-(1H-imidazol-1-ylmethyl)-1,3-dioxolan-4-ylmethoxy]phenyl}-2-propylpyrimidine dinitrate; mp. 169° C;

cis-4-{4-[2-(2,4-dichlorophenyl)-2-(1H-imidazol-1-ylmethyl)-1,3-dioxolan-4-ylmethoxy]phenyl}-2-(1-methylethyl)pyrimidine dinitrate; mp. 178° C; and cis-4-{2-[2-(2,4-dichlorophenyl)-2-(1H-imidazol-1-ylmethyl)-1,3-dioxolan-4-ylmethoxy]phenyl}-2-phenylpyrimidine dinitrate. monohydrate; mp. 161.7° C.

EXAMPLE XXII

To a stirred sodium ethanolate solution, previously prepared starting from 0.5 parts of sodium and 80 parts of ethanol, are added first 2 parts of guanidine hydrochloride and then after 10 minutes, 5 parts of cis-1-{4-[2-(2,4-dichlorophenyl)-2-(1H-imidazol-1-yl-methyl)-1,3-dioxolan-4-ylmethoxy]phenyl}-3-(dimethylamino)-2-propen-1-one. The whole is stirred and refluxed overnight. Water is added to the reaction mixture and the product is precipitated. It is filtered off and crystallized from a mixture of N,N-dimethylformamide and water, yielding 4.3 parts (86%) of cis-4-{4-[2-(2,4-dichlorophenyl)-2-(1H-imidazol-1-ylmethyl)-1,3-dioxolan-4-ylmethoxy]phenyl}-2-pyrimidinamine; mp. 241.4° C.

In a similar manner there are also prepared:

cis-4-[2-(2,4-dichlorophenyl)-2-(1H-imidazol-1-ylmethyl)-1,3-dioxolan-4-ylmethoxy]phenyl}-N-methyl-2-pyrimidinamine; mp. 175.9° C.; and cis-4-{4-[2-(2,4-dichlorophenyl)-2-(1H-imidazol-1-ylmethyl)-1,3-dioxolan-4-ylmethoxy]phenyl}-N-ethyl-2-pyrimidinamine; mp. 163.2° C.

EXAMPLE XXIII

To a stirred solution of 0.8 parts of sodium hydride dispersion 78% in 80 parts of 2-propanol are added 1.7 parts of N-propylguanidine sulfate (2:1). After stirring for 30 minutes at room temperature, 5 parts of cis-1-{4-[2-(2,4-dichlorophenyl)-2-(1H-imidazol-1-ylmethyl)-1,3-dioxolan-4-ylmethoxy]phenyl}-3-(dimethylamino)-2-propen-1-one are added. The whole is stirred and refluxed overnight. The reaction mixture is cooled, water is added and the product is extracted twice with trichloromethane. The combined extracts are dried, filtered and evaporated. The residue is converted into the nitrate salt is filtered off and crystallized from a mixture of ethanol and 2,2'-oxybispropane, yielding 4 parts (60%) of cis-4-{4-[2-(2,4-dichlorophenyl)-2-(1H-imidazol-1-ylmethyl)-1,3-dioxolan-4-ylmethoxy]phenyl}-N-propyl-2-pyrimidinamine dinitrate; mp. 170.3° C.

In a similar manner there are also prepared:

cis-4-{4-[2-(2,4-dichlorophenyl)-2-(1H-imidazol-1-ylmethyl)-1,3-dioxolan-4-ylmethoxy]phenyl}-N-(1-methylethyl)-2-pyrimidinamine dinitrate; mp. 164.3° C.;

cis-N-butyl-4-{4-[2-(2,4-dichlorophenyl)-2-(1H-imidazol-1-ylmethyl)-1,3-dioxolan-4-ylmethoxy]phenyl}-2-pyrimidinamine dinitrate monohydrate; mp. 167.2° C.;

cis-4-}4-[2-(2,4-dichlorophenyl)-2-(1H-imidazol-1-ylmethyl)-1,3-dioxoland-4-ylmethoxy]phenyl}-N-(2-methylpropyl)-2-pyrimidinamine dinitrate; mp. 183.2° C.;

cis-4-{4-[2-(2,4-dichlorophenyl)-2-(1H-imidazol-1-ylmethyl)-1,3-dioxolan-4-ylmethoxy]phenyl}-N-(3-methylbutyl)-2-pyrimidinamine dinitrate; mp. 173.2° C.;

cis-N-cyclohexyl-4-{4-[2-(2,4-dichlorophenyl)-2-(1H-imidazol1-ylmethyl)-1,3-dioxolan-4-ylmethoxy]phenyl}-2-pyrimidinamine dinitrate; mp. 201.3° C.;

cis-4-{4-[2-(2,4-dichlorophenyl)-2-(1H-imidazol-1-ylmethyl)-1,3-dioxolan-4-ylmethoxy]phenyl}-N-phenyl-2-pyrimidinamine; mp. 160° C.;

cis-4-{4-[2-(2,4-dichlorophenyl)-2-(1H-imidazol-1-ylmethyl)-1,3-dioxolan-4-ylmethoxy]phenyl}-N,N-dimethyl-2-pyrimidinamine dinitrate; mp. 179.6° C.; and cis-4-{4-[2-(2,4-dichlorophenyl)-2-(1H-imidazol-ylmethyl)-1,3-dioxolan-4-ylmethoxy]phenyl }-N,N-diethyl-2-pyrimidinamine dinitrate; mp. 173.6° C.

EXAMPLE XXIV

5 Parts of urea and 5 parts of cis-1-{4-[2-(2,4-dichlorophenyl)-2-(1H-imidazol-1-ylmethyl)-1,3-dioxolan-4-ylmethoxy]phenyl}-3-(dimethylamino)-2-propen-1-one are heated under I.R.-radiation for 3 hours. The resulting melt is cooled and water and 4-methyl-2-pentanone are added. The precipitated product is filtered off and crystallized from a mixture of N,N-dimethylformamide and water (activated charcoal), yielding 1.7 parts (34%) of cis-4-{4-[2-(2,4-dichlorophenyl)-2-(1H-imidazol-1-ylmethyl)-1,3-dioxolan-4-ylmethoxy]phenyl}-2-pyrimidinol; mp. 243.4° C.

EXAMPLE XXV

5 Parts of thiourea and 1.5 parts of cis-1-{4-[2-(2,4-dichlorophenyl)-2-(1H-imidazol-1-ylmethyl)-1,3-dioxolan-4-ylmethoxy]phenyl}-3-(dimethylamino)-2-propen-1-one are melted together under I.R.-radiation for one hour. To the resulting melt are added water and 4-2-pentanone. The precipitated product is filtered off and crystallized from ethanol, yielding 1.4 parts (27%) of cis-4-{4-[2-(2,4-dichlorophenyl)-2-(1H-imidazol-1-ylmethyl)1,3-dioxolan-4-ylmethoxy]phenyl}-2(1H)pyrimidinethione; mp. 207.5° C.

EXAMPLE XXVI

A mixture of 2 parts of dimethyl sulfate, 4 parts of cis-4-{4-[2-(2,4-dichlorophenyl)-2-(1H-imidazol-1-ylmethyl)-1,3-dioxolan-4-ylmethoxy]phenyl}-2(1H)-pyrimidinethione, 0.75 parts of sodium hydroxide solution 50% and 80 parts of ethanol is stirred overnight at room temperature. Water is added and the product is extracted twice with 1,1'-oxybisethane. The combined ixtracts are dried, filtered and evaporated. The residue is purified by column-chromatography over silica gel using a mixture of trichloromethane and methanol (98:2 by volume) as eluent. The pure fractions are collected and the eluent is evaporated. The residue is converted into the nitrate salt in 4-methyl-2-pentanone. The salt is filtered off and crystallized from a mixture of ethanol and 2,2'-oxybispropane, yielding 2.3 parts (39%) of cis-4-{4-[2-(2,4-dichlorophenyl)-2-(1H-imidazol-1-ylmethyl)-1,3-dioxolan-4-ylmethoxy]phenyl}-2-(methylthio)pyrimidine mononitrate; mp. 187.6° C.

EXAMPLE XXVII

A mixture of 2 parts of bromoethane, 4 parts of cis-4-{4-[2-(2,4-dichlorophenyl)-2-(1H-imidazol-1-ylmethyl)-1,3-dioxolan-4-ylmethoxy]phenyl}-2(1H)pyrimidinethione, 0.45 parts of sodium hydroxide solution 50% and 80 parts of ethanol is stirred overnight at room temperature. Water is added and the product is extracted twice with 1,1'-oxybisethane. The combined extracts are dried, filtered and evaporated. The residue is purified by column-chromatography over silica gel using trichloromethane as eluent. The pure fractions are collected and the eluent is evaporated. The residue is converted into the nitrate salt in 4-methyl-2-pentanone. The product is filtered off and crystallized from a mixture of ethanol and 2,2'-oxybispropane, yielding 2.9 (56%) of cis-4-{4-[2-(2,4-dichlorophenyl)-2-(1H-imidazol-1-ylmethyl)-1,3-dioxolan-4-ylmethoxy]phenyl}-2-(ethylthio)pyrimidine dinitrate; mp. 150.7° C.

In a similar manner there are also prepared:

cis-4-{4-[2-(2,4-dichlorophenyl)-2-(1H-imidazol-1-ylmethyl)-1,3-dioxolan-4-ylmethoxy]phenyl}-2-(propylthio)pyrimidine mononitrate; mp. 146.6° C.; and cis-2-(butylthio)-4-[2-(2,4-dichlorophenyl)-2-(1H-imidazol-1-ylmethyl)-1,3-dioxolan-4-ylmethoxy]phenyl}pyrimidine dinitrate; mp. 147.8° C.

EXAMPLE XXVIII

To a stirred mixture of 4.9 parts of cis-4-{4-[2-(2,4-dichlorophenyl)-2-(1H-imidazol-1-ylmethyl)-1,3-dioxolan-4-ylmethoxy]phenyl}-2-pyrimidinamine and 75 parts of pyridine are added dropwise 1.1 parts of propanoyl chloride. Upon completion, stirring is continued for 1 hour at reflux temperature. The reaction mixture is cooled and poured onto water. The precipitated product is filtered off, washed with water and dried, yielding 5.5 parts of cis-N-[4-{4-[2-(2,4-dichlorophenyl)-2-(1H-imidazol-1-ylmethyl)1,3-dioxolan-4-ylmethoxy]phenyl}-2-pyrimidinyl]propanamide; mp. 221.5° C.

In a similar manner there are prepared:

cis-N[4-{4-[2-(2,4-dichlorophenyl)-2-(1H-imidazol-1-ylmethyl-1,3-dioxolan-4-ylmethoxy]phenyl}-2-pyrimidinyl]acetamide; mp. 226.9° C.;

cis-N-[4-{4-[2-(2,4-dichlorophenyl)-2-(1H-imidazol-1-ylmethyl)-1,3-dioxolan-4-ylmethoxy]phenyl}-2-pyrimidinyl]butanamide; mp. 189.1° C.;

cis-N-[4-{4-[2-(2,4-dichlorophenyl)-2-(1H-imidazol-1-ylmethyl)-1,3-dioxolan-4-ylmethoxy]phenyl}-2-pyrimidinyl]pentanamide; mp. 191.9° C.; and cis-N-[4-{4-[2-(2,4-dichlorophenyl)-2-(1H-imidazol-1-ylmethyl)-1,3-dioxolan-4-ylmethoxy]phenyl}-2-pyrimidinyl]-3-methylbutanamide; mp. 184.7° C.

EXAMPLE XXIX

A mixture of 1.4 parts of N,N-dimethyl-4-pyridinamine and 45 parts of benzene is distilled azeotropically to dry. After cooling, there are added successively 100 parts of pyridine and 4.98 parts of cis-4-{4-[2-(2,4-dichlorophenyl)-2-(1H-imidazol-1-ylmethyl)-1,3dioxolan-4-ylmethoxy]phenyl}-2-pyrimidinamine. Then there are added dropwise 1.7 parts of benzoyl chloride. Upon completion, stirring is continued for 4 hours at reflux temperature. The reaction mixture is cooled and poured onto water. The product is extracted with benzene. The extract is washed with water, dried, filtered and evaporated. The residue is purified by column-chromatography over silica gel using a mixture of trichloromethane and methanol (98:2 by volume) as eluent. The pure fractions are collected and the eluent is evaporated. The residue is crystallized from 4-methyl-2-pentanone. The product is filtered off and dried in vacuo for 36 hours at 130° C., yielding 2.8 parts of cis-N-[4-{4-[2-(2,4-dichlorophenyl)-2-(1H-imidazol-1-ylmethyl)-1,3-dioxolan-4-ylmethoxy]phenyl}-2-pyrimidinyl]benzamide; mp. 163° C.

In a similar manner there is also prepared:

cis-N-[4-{4-[2-(2,4-dichlorophenyl)-2-(1H-imidazol-1-ylmethyl)-1,3-dioxolan-4-ylmethoxy]phenyl}-2-pyrimidinyl]-4-fluorobenzamide; mp. 151.2° C.

EXAMPLE XXX

To 160 parts of 1-butanol are added 1.8 parts of sodium hydride dispersion 75% and the whole is stirred for 15 minutes at room temperature. Then there are added 4.6 parts of guanidine hydrochloride (2:1) and stirring is continued for 30 minutes at room temperature. 12.5 Parts of cis-1-[4-[2-(2,4- dichlorophenyl)-2-(1H-1,2,4-triazol-1-ylmethyl)-1,3-dioxolan-4-ylmethoxy]phenyl]-3-(dimethylamino)-2-propen-1-one are added and the whole is stirred and refluxed for 4 hours. The reaction mixture is evaporated and water is added to the residue. The product is extracted with dichloromethane. The extract is washed with water, dried, filtered and evaporated. The residue is crystallized from 1-butanol. The product is filtered off and dried, yielding 7 parts (56.1%) of cis-4-{4-[2-(2,4-dichlorophenyl)-2-(1H-1,2,4-triazol-1-ylmethyl)-1,3-dioxolan-4-ylmethoxy[-phenyl}-2-pyrimidinamine; mp. 208.3° C.

In a similar manner there are also prepared:

cis-4-{4-[2-(2,4-dichlorophenyl)-2-(1H-1,2,4-triazol-1-ylmethyl)1,3-dioxolan-4-ylmethoxy]phenyl}-N-ethyl-2-pyrimidinamine; mp. 154.6° C.;

cis-4-{4-[2-(2,4-dichlorophenyl)-2-(1H-1,2,4-triazol-1-ylmethyl)-1,3-dioxolan-4-ylmethoxy]phenyl}-N-propyl-2-pyrimidinamine; mp. 139.6° C.;

cis-4-{4-[2-(2,4-dichlorophenyl)-2-(1H-1,2,4-triazol-1-ylmethyl)-1,3-dioxolan-4-ylmethoxy]phenyl}-N,N-dimethyl-2-pyrimidinamine; mp. 164.3° C.; and cis-4-{4-[2-(2,4-dichlorophenyl)-2-(1H-1,2,4-triazol-1-ylmethyl)-1,3-dioxolan-4-ylmethoxy]phenyl}-N,N-diethyl-2-pyrimidinamine hemihydrate; mp. 143.5° C.

EXAMPLE XXXI

To a stirred mixture of 5 parts of cis-4-{4-[2-(2,4-dichlorophenyl)-2-(1H-1,2,4-triazol-1-ylmethyl)-1,3-dioxolan-4-ylmethoxy]phenyl}-2-pyrimidinamine and 100 parts of dry pyridine are added dropwise 0.86 parts of acetyl chloride. Upon completion, the whole is stirred and refluxed for 30 minutes. The reaction mixture is cooled and poured onto water. The precipitated product is filtered off and crystallized from 4-methyl-2-pentanone, yielding 3.5 parts of cis-N-[4-{4-[2-(2,4-dichlorophenyl)-2-(1H-1,2,4-triazol-1-ylmethyl)-1,3-dioxolan-4-ylmethoxy]phenyl}-2-pyrimidinyl]acetamide; mp. 217.4°–219.8° C.

In a similar manner there are also prepared:

cis-N-[4-{4-[2-(2,4-dichlorophenyl)-2-(1H-1,2,4-triazol-1-ylmethyl)-1,3-dioxolan-4-ylmethoxy]phenyl}-2-pyrimidinyl]propanamide; mp. 233.8° C.;

cis-N-[4-{4-[2-(2,4-dichlorophenyl)-2-(1H-1,2,4-triazol-1-ylmethyl)-1,3-dioxolan-4-ylmethoxy]phenyl}-2-pyrimidinyl]butanamide; mp. 193.7° C.; and cis-N-[4-{4-[2-(2,4-dichlorophenyl)-2-(1H-1,2,4-triazol-1-ylmethyl)-1,3-dioxolan-4-ylmethoxy]phenyl}-2-pyrimidinyl]pentanamide; mp. 167° C.

EXAMPLE XXXII

A mixture of 1 part of hydroxylamine hydrochloride, 5 parts of cis-1-{4-[2-(2,4-dichlorophenyl)-2-(1H-imidazol-1-ylmethyl)-1,3dioxolan-4-ylmethoxy]-phenyl}-3-(dimethylamino)-2-propen-1-one, 80 parts of methanol is stirred and refluxed for one week. The solvent is evaporated and the residue is purified by column-chromatography over silica gel using trichloromethane as eluent. The pure fractions are collected and the eluent is evaporated. The residue is crystallized from a mixture of 4-methyl-2-pentanone and 2,2'-oxybispropane. The product is filtered off and dried, yielding 2 parts (42%) of cis-1-{2-(2,4-dichlorophenyl)-4-[4-(5-isoxazolyl)phenoxymethyl]-1,3-dioxolan-2-ylmethyl}-1H-imidazole; mp. 143.5° C.

EXAMPLE XXXIII

A mixture of 2 parts of hydrazine hydrate, 5 parts of cis-1-{4-[2-(2,4-dichlorophenyl)-2-(1H-imidazol-1- ylmethyl)-1,3-dioxolan-4-ylmethoxy]phenyl}-3-(dimethylamino)-2-propen-1-one and 80 parts of 1-butanol is stirred and refluxed for 3 hours. The reaction mixture is evaporated in vacuo. The residue is triturated in 4-methyl-2-pentanone. The product is filtered off and crystallized from ethanol, yielding 3.6 parts (76%) of cis-3-{4-[2-(2,4-dichlorophenyl)-2-(1H-imidazol-1-ylmethyl)-1,3-dioxolan-4-ylmethoxy]phenyl}-1H-pyrazole; mp. 191.9° C.

In a similar manner there are prepared:

cis-5-{4-[2-(2,4-dichlorophenyl)-2-(1H-imidazol-1-ylmethyl)-1,3-dioxolan-4-ylmethoxy]phenyl}-1-methyl-1H-pyrazole dinitrate; mp. 144.1° C.;

cis-5-{4-[2-(2,4-dichlorophenyl)-2-(1 H-imidazol-1-ylmethyl)-1,3-dioxolan-4-ylmethoxy]phenyl}-1-phenyl-1H-pyrazole ethanedioate (1:1); mp. 187.1° C.; and cis-5-{4[2-(2,4-dichlorophenyl)-2-(1H-imidazol-1-ylmethyl)-1,3-dioxolan-4-ylmethoxy]phenyl}-1H-pyrazole-1-ethanol; mp. 123.2° C.

EXAMPLE XXXIV

To a stirred mixture of 3 parts of 4-(1-methyl-1H-imidazol-4-yl)phenol and 100 parts of dimethyl sulfoxide are added 0.64 parts of sodium hydride dispersion 78%. After stirring till foaming has ceased, 7.22 parts of cis-2-(2,4-dichlorophenyl)-2-(1H-imidazol-1-ylmethyl)-1,3-dioxolan-4-ylmethyl methanesulfonate are added. The whole is heated slowly to 100° C. and stirring is continued for 6 hours at this temperature. The reaction mixture is evaporated and the solid residue is dissolved in trichloromethane. The solution is washed a few times with water, dried, filtered and evaporated. The solid residue is purified by column-chromatography over silica gel using a mixture of trichloromethane and methanol (95:5 by volume) as eluent. The pure fractions are collected and the eluent is evaporated. The residue is crystallized from 2-propanol. The product is filtered off and dried, yielding 5.5 parts (66%) of cis-4-{4-[2-(2,4-dichlorophenyl)-2-(1H-imidazol-1-ylmethyl)-1,3-dioxolan-4-ylmethoxy]phenyl}-1-methyl-1H-imidazole; mp. 184° C.

In a similar manner there are also prepared:

cis-5-{4-[2-(2,4-dichlorophenyl)-2-(1H-imidazol-1-ylmethyl)-1,3-dioxolan-4-ylmethoxy]phenyl}-1-ethyl-1H-imidazole dinitrate; mp. 198.5° C.;

cis-5-{4-[2-(2,4-dichlorophenyl)-2-(1H-imidazol-1-ylmethyl)-1,3-dioxolan-4-ylmethoxy]phenyl}-1-propyl-1H-imidazole dinitrate; mp. 161.9° C.;

cis-5-{4-[2-(2,4-dichlorophenyl)-2-(1 H-imidazol-1-ylmethyl)-1,3-dioxolan-4-ylmethoxy]phenyl}-1-(1-methylethyl)-1H-imidazlole dinitrate; mp. 189.7° C.;

cis-1-butyl-5-{4-[2-(2,4-dichlorophenyl)-2-(1H-imidazol-1-ylmethyl)-1,3-dioxolan-4-ylmethoxy]phenyl}-1H-imidazole dinitrate monohydrate; mp. 160.8° C.;

cis-5-{4-[2-(2,4-dichlorophenyl)-2-(1H-imidazol-1-ylmethyl)-1,3-dioxolan-4-ylmethoxy]phenyl}-1-(2-methylpropyl)-1H-imidazole dinitrate monohydrate; mp. 202.5° C.;

cis-4-{4-[2-(2,4-dichlorophenyl)-2-(1H-imidazol-1-ylmethyl)-1,3-dioxolan-4-ylmethoxy]phenyl}-1-ethyl-2-(methylthio)-1H-imidazole ethanedioate (2:3) monohydrate; mp. 128.8° C.;

cis-4-{4-[2-(2,4-dichlorophenyl)-2-(1H-imidazol-1-ylmethyl)-1,3-dioxolan-4-ylmethoxy]phenyl}-1-ethyl-2-(ethylthio)-1H-imidazole ethanedioate (1:2); mp. 105° C.;

cis-4-{4-[2-(2,4-dichlorophenyl)-2-(1H-imidazol-1-ylmethyl)-1,3-dioxolan-4-ylmethoxy]phenyl}-2-(ethylthio)-1-methyl-1H-imidazole ethanedioate (1:1); mp. 196.9° C.;

cis-5-{4-[2-(2,4-dichlorophenyl)-2-(1-ylmethyl)-1,3-dioxolan-4-ylmethoxy]phenyl}-1-methyl-1H-imidazole dinitrate; mp. 194.8° C.;

cis-4-{4-[2-(2,4-dichlorophenyl)-2-(1H-imidazol-1-ylmethyl)-1,3-dioxolan-4-ylmethoxy]phenyl}-1-ethyl-1H-imidazole dinitrate dihydrate; mp. 126.2° C.;

cis-4-{4-[2-(2,4-dichlorophenyl)-2-(1 H-imidazol-1-ylmethyl)-1,3-dioxolan-4-ylmethoxy]phenyl}-1-propyl-1H-imidazole ethanedioate (1:2); mp. 154.5° C.;

cis-4-{4-[2-(2,4-dichlorophenyl)-2-(1H-imidazol-1-ylmethyl)-1,3-dioxolan-4-ylmethoxy]phenyl}-1-(1-methylethyl)-1H-imidazole ethanedioate (2:5); mp. 164.7° C.;

cis-1-butyl-4-{4-[2-(2,4-dichlorophenyl)-2-(1H-imidazol-1-ylmethyl)-1,3-dioxolan-4-ylmethoxy]phenyl}-1H-imidazole; mp. 109.4° C.;

cis-4-{4-[2-(2,4-dichlorophenyl)-2-(1H-imidazol-1-ylmethyl)-1,3-dioxolan-4-ylmethoxy]phenyl}-1-(phenylmethyl)-1H-imidazole; mp. 134.9° C.;

cis-2-{4-[2-(2,4-dichlorophenyl)-2-(1H-imidazol-1-ylmethyl)-1,3-dioxolan-4-ylmethoxy]phenyl}-1-ethyl-1H-imidazole dihydrochloride; mp. 221.2° C.;

cis-5-4-[2-(2,4-dichlorophenyl)-2-(1H-imidazol-1-ylmethyl)-1,3-dioxolan-4-ylmethoxy]phenyl-1-(methylthio)-1H-imidazole dinitrate; mp. 154.1° C.

cis-5-{4-[2-(2,4-dichlorophenyl)-2-(1H-imidazol-1-ylmethyl)-1,3-dioxolan-4-ylmethoxy]phenyl}-1-ethyl-2-(methylthio)-1H-imidazole dinitrate; mp. 162.9° C.; and cis-5-{4-[2-(2,4-dichlorophenyl)-2-(1H-imidazol-1-ylmethyl)-1,3-dioxolan-4-ylmethoxy]phenyl}-2-(methylthio)-1-propyl-1H-imidazole dinitrate; mp. 147.8° C.

EXAMPLE XXXV

To a stirred solution of 2.3 parts of 4-(2-methyl-4-thiazoly)phenol and 0.4 parts of sodium hydride dispersion 78% in 90 parts of N,N-dimethylformamide are added 4.2 parts of cis-2-(2,4-dichlorophenyl)-2-(1H-imidazol-1-ylmethyl)-1,3-dioxolan-4-ylmethyl methanesulfonate. Stirring is continued for 6 hours at 100° C. The reaction mixture is cooled and poured onto water. The product is extracted twice with trichloromethane. The combined extracts are washed with water, dried, filtered and evaporated. The residue is crystallized from 4-methyl-2-pentanone. The product is filtered off and dried, yielding 4 parts (80%) of cis-1-{2-(2,4-dichlorophenyl)-4-[4-(2-methyl-4-thiazolyl)phenoxymethyl]-1,3-dioxolan-2-ylmethyl}-1H-imidazole; mp. 174° C.

In a similar manner are prepared:

cis-1-[2-(2,4-dichlorophenyl)-4-{[4-(2-thiazolyl)phenoxy]methyl}-1,3-dioxolan-2-ylmethyl]-1H-imidazole; mp. 154.8° C.; and cis-1-{2-(2,4-dichlorophenyl)-4-[4-(4-methyl-2-thiazoly)phenoxymethyl]-1,3-dioxolan-2-ylmethyl}-1H-imidazole ethanedioate (1:2); mp. 180.8° C.

EXAMPLE XXXVI

To a stirred suspension of 1.8 parts of 4-(1,3,4-oxadiazol-2-yl)phenol and 0.4 parts of sodium hydride dispersion 78% in 100 parts of dimethyl sulfoxide are added 4.2 parts of cis-2-(2,4-dichlorophenyl)-2-(1H-imidazol-1-ylmethyl)-1,3-dioxolan-4-ylmethyl methanesulfonate. When hydrogen gas evolution has ceased, stirring is continued overnight at 100° C. The reaction mixture is cooled, poured onto water and the precipitated product is filtered off. It is crystallized from 4-methyl-2-pentanone, yielding 3.7 parts (78%) of cis-2-{4-[2-(2,4-dichlorophenyl)-2-(1H-imidazol-1-ylmethyl)-1,3-dioxolan-4-ylmethoxy]phenyl}-1,3,4-oxadiazole; mp. 181° C.

Similar manner there is also prepared:
cis-2-{4-[2-(2,4-dichlorophenyl)-2-(1H-imidazol-1-ylmethyl)-1,3-dioxolan-4-ylmethoxy]phenyl}-5-methyl-1,3,4-oxadiazole; mp. 162.9° C.

EXAMPLE XXXVII

A mixture of 1.3 parts of 4-(2-oxazolyl)phenol, 3.1 parts of cis-2-(2,4-dichlorophenyl)-2-(1H-imidazol-1-ylmethyl)-1,3-dioxolan-4-ylmethyl methanesulfonate, 2 parts of potassium carbonate and 68 parts of N,N-dimethylformamide is stirred for 4 hours at 100° C. The reaction mixture is cooled and poured onto water. The product is extracted twice with 1,1'-oxybisethane. The combined extracts are washed with water, dried, filtered and evaporated. The residue is crystallized from 4-methyl-2-pentanone. The product is filtered off and dried, yielding 2.3 parts (65%) of cis-1-{2-(2,4-dichlorophenyl)-4-[4-(2-oxazolyl)phenoxymethyl]-1,3-dioxolan-2-ylmethyl}-1H-imidazole; mp. 162.3° C.

EXAMPLE XXXVIII

A mixture of 2.2 parts of 1-[(isocyanomethyl)sulfonyl]-4-methylbenzene, 5 parts of cis-4-[2-(2,4-dichlorophenyl)-2-(1H-imidazol-1-ylmethyl)-1,3-dioxolan-4-ylmethoxy]benzaldehyde nitrate, 2 parts of potassium carbonate and 80 parts of methanol is stirred and refluxed overnight. The reaction mixture is cooled and water is added. The product is extracted twice with 1,1'-oxybisethane. The combined extracts are washed with water, dried, filtered and evaporated. The residue is purified by column-chromatography over silica gel using a mixture of trichloromethane and methanol (99:1 by volume) as eluent. The pure fractions are collected and the eluent is evaporated. The residue is crystallized from 4-methyl-2-pentanone. The product is filtered off and dried, yielding 2.2 parts (47%) of cis-1-[2-(2,4-dichlorophenyl)-4-{[4-(5-oxazolyl)phenoxy]methyl}-1,3-dioxalan--2-ylmethyl]-1H-imidazole; mp. 146.1° C.

EXAMPLE XXXIX

To a stirred mixture of 2.1 parts of 4-(5-methyl-1,3,4-oxadiazol-2-yl)phenol and 75 parts of dimethyl sulfoxide are added 0.6 parts of sodium hydride dispersion 50%. After stirring for 30 minutes at 40° C., the mixture is cooled and 4.1 parts of cis-[2-(2,4-dichlorophenyl)-2-(1H-1,2,4-triazol-1-ylmethyl)-1,3-dioxolan-4-ylmethyl]methanesulfonate are added. The whole is stirred and heated for 6 hours at 80° C. The reaction mixture is cooled and poured onto water. The product is extracted with benzene. The extract is washed with water, dried, filtered and evaporated, yielding 1.9 parts of cis-2-{4-[2-(2,4-dichlorophenyl)-2-(1H-1,2,4-triazol-1-ylmethyl)-1,3-dioxolan-4-ylmethoxy]phenyl}-5-methyl-1,3,4-oxadiazole; mp. 178.1° C.

Following the same procedure and using equivalent amounts of the appropriate starting materials there is also prepared:

cis-1-[2-(2,4-dichlorophenyl)-4-{[4-(1,3,4-oxadiazol-2-yl)-phenoxy]methyl}-1,3-dioxolan-2-ylmethyl]-1H-1,2,4-triazole; mp. 232.3° C.

EXAMPLE XL

To a stirred solution of 3 parts of 4-(1methyl-1H-imidazol-5-yl)phenol in 100 parts of dimethyl in 100 parts of dimethyl sulfoxide and 90 parts of benzene are added 0.5 parts of sodium hydride dispersion 50% and the whole is stirred at 50° C. till foaming has ceased. Then there are added 4 parts of cis-1-[2-(2,4-dichlorophenyl)-2-(1H-1,2,4-triazol-1-ylmethyl)-1,3-dioxolan-4-ylmethyl]methanesulfonate and stirring is continued for 3 hours at 80° C. The reaction mixture is poured onto water and the product is extracted with 4-methyl- b 2-pentanone, with benzene and again with 4-methyl-2-pentanone. The combined extracts are washed with water, with 5% sodium hydroxide solution and twice with water, dried, filtered and evaporated. The residue is converted into the nitrate salt in 2-propanone. The salt is filtered off and crystallized from ethanol, yielding 4.1 parts of cis-1-{2-(2,4-dichlorophenyl)-4-[4-(1-methyl-1H-imidazol-5-yl)phenoxymethyl]-1,3-dioxolan-2-ylmethyl}-1H-1,2,4-triazole mononitrate; mp. 200.2° C.

Following the same procedure and using equivalent amounts of the appropriate starting materials there are also prepared:

cis-1-[2-(2,4-dichlorophenyl)-4-{4-[1-ethyl-2-(methylthio)-1H-imidazol-5-yl]phenoxymethyl}-1,3-dioxolan-2-ylmethyl]-1H-1,2,4-triazole mononitrate; mp. 151.6° C.;

cis-1-{2-(2,4-dichlorophenyl)-4-[4-(1-ethyl-1H-imidazol-5-yl)phenoxymethyl]-1,3-dioxolan-2-ylmethyl}-1H-1,2,4-triazole dinitrate; mp. 170° C.;

cis-1-[2-(2,4-dichlorophenyl)-4-[1-methyl-2-(methylthio)-1H-imidazol-5-yl]phenoxymethyl}-1,3-dioxolan-2-ylmethyl]-1H-1,2,4-triazole dinitrate; mp. 124.7° C.;

cis-1-[2-(2,4-dichlorophenyl)-4-{4-[2-(methylthio)-1-propyl-1H-imidazol-5-yl]phenoxymethyl}-1,3-dioxolan-2-ylmethyl]-1H-1,2,4-triazole mononitrate; mp. 129.2° C.; and cis-1-{2-(2,4-dichlorophenyl)-4-[4-(1-propyl-1H-imidazol-5-yl)-phenoxymethyl]-1,3-dioxolan-2-ylmethyl}-1H-1,2,4-triazole mononitrate; mp. 187.9° C.

EXAMPLE XLI

Following the procedure of Example 1 and using equivalent amounts of the appropriate starting materials there are also prepared:

trans-1-{4-[2-(2,4-dichlorophenyl)-2-(1H-imidazol-1-ylmethyl)-1,3-dioxolan-4-ylmethoxy]phenyl}-3-(dimethylamino)-2-propen-1-one;

1-{4-[2-(2,4-dichlorophenyl-2-(1H-imidazol-1-ylmethyl)-1,3-dioxolan-4-ylmethoxy]phenyl}-3-(dimethyl mino)-2-propen-1-one;

trans-1-{4-[2-(2,4-dichlorophenyl)-2-(1H-1,2,4-triazol-1-yl- methyl)-1,3-dioxolan-4-ylmethoxy]phenyl}-3-(dimethylamino)-2-propen-1-one;

1-{2-(2,4-dichlorophenyl)-2-(1H-1,2,4-triazol-1-ylmethyl)-1,3-dioxolan-4-ylmethoxy]phenyl}-3-(dimethylamino)-2-propen-1-one;

1-{4-[2-(2-bromophenyl)-2-(1H-imidazol-1-ylmethyl)-1,3-dioxolan-4-ylmethoxy]phenyl}-3-(dimethylamino)-2-propen-1-one;

3-(dimethylamino)-1-{4-[2-(4-fluorophenyl)-2-(1H-imidazol-1yl-methyl)-1,3-dioxolan-4-ylmethoxy]-phenyl}-2-propen-1-one;

3-(dimethylamino)-1-{2-(1H-imidazol-1-ylmethyl)-2-(4-methylphenyl)-1,3-dioxolan-4-ylmethoxy]phenyl}-2-propen-1one;

3-(dimethylamino)-1-{-4-[2-(1H-imidazol-1-ylmethyl)-2-(4-methoxyphenyl)-1,3-dioxolan-4-yimethoxy]phenyl }-2propen-1-one;

1-{4-[2-(4-bromo-2-methylphenyl)-2-(1H-imidazol-1-ylmethyl)-1,3-dioxolan-4-ylmethoxy]phenyl}-3-(dimethylamino)-2-propen-1-one;

1-{4-[2-(2-chloro-4-methoxyphenyl)-2-(1H-imidazol-1-ylmethyl)-1,3-dioxolan-4-ylmethoxy]phenyl}-3-(dimethylamino)-2-propen-1-one;

1-{4-[2-(4-bromophenyl)-2-(1H-1,2,4-triazol-1-ylmethyl)-1,3-dioxolan-4-ylmethoxy]phenyl}-3-(dimethylamino)-2-propen-1-one;

1-{4-[2-(2-chloro-4-methylphenyl)-2-(1H-1,2,4-triazol-1-ylmethyl)-1,3-dioxolan-4-ylmethoxy]phenyl}-3-(dimethylamino)-2-propen-1-one;

3-(dimethylamino)-1-{4-[2-(1H-imidazol-1-ylmethyl)-2-(2-thienyl)-1,3-dioxolan-4-ylmethoxy]phenyl}-2-propen-1one;

1-{4-[2-(5-chloro-2-thienyl)-2-(1H-imidazol-1-ylmethyl)-1,3-dioxolan-4-ylmethoxy]phenyl}-3-(dimethylamino)-2-propen-1-one;

1-{4-[2-(5-bromo-2-thienyl)-2-(1H-1,2,4-triazol-1-ylmethyl)-1,3-dioxolan-4-ylmethoxy]phenyl}-3-(dimethylamino)-2-propen-1-one;

3-(dimethylamino)-1-{4-[2-(2-thienyl)-2-(1H-1,2,4-triazol-1-ylmethyl)-1,3-dioxolan-4-ylmethoxy]phenyl}-2-propen-1-one.

EXAMPLE XLII

Following procedure of Example XX and using equivalent amounts of the appropriate starting materials these are also prepared:

trans-4-{4-[2-(2,4-dichlorophenyl)-2-(1H-imidazol-1-ylmethyl)-1,3-dioxolan-4-ylmethoxy]phenyl}pyrimidine;

4-{4-[2-(4-bromo-2-methylphenyl)-2-(1H-imidazol-1-ylmethyl)-1,3-dioxolan-4-ylmethoxy]phenyl}-2-methylpyrimidine; 4-{4-[2-(1H-imidazol-1-ylmethyl)-(2-thienyl)-1,3-dioxolan-4-yl-methoxy]phenyl}pyrimidine;

cis-2-butyl-4-{4-[2-(5-chloro-2-thienyl)-2-(1H-imidazol-1-ylmethyl)-1,3-dioxolan-4-ylmethoxy]phenyl}pyrimidine;

4-{4-[2-(4-bromophenyl)-2-(1H-1,2,4-triazol-1-ylmethyl)-1,3-dioxolan-4-ylmethoxy]phenyl}-pyrimidine;

4-{4-[2-(2-chloro-4-methylphenyl)-2-(1H-1,2,4-triazol-1-ylmethyl)-1,3-dioxolan-4-ylmethoxy]phenyl}-2-methylpyrimidine;

4-{4-[2-(5-bromo-2-thienyl)-2-(1H-1,2,4-triazol-1-ylmethyl)-1,3-dioxolan-4-ylmethoxy]phenyl}pyrimidine;

2-propyl-4-{4-[2-(2-thienyl)-2-(1H-1,2,4-triazol-1-ylmethyl)-1,3-dioxolan-4-ylmethoxy]phenyl}pyrimidine.

EXAMPLE XLIII

Following the procedure of Example XXX and using equivalent amounts of the appropriate starting materials there are also prepared:

trans-4-{4-[2-(2,4-dichlorophenyl)-2-(1H-imidazol-1yl-methyl)-1,3-dioxolan-4-ylmethoxy]phenyl}-2-pyrimidinamine;

4-{4-[2-(1H-imidazol-1-ylmethyl)-2-(4-methylphenyl)-1,3-dioxolan-4-ylmethoxy]phenyl}-N-(2-phenylethyl)-2-pyrimidinamine;

4{4-[2-(1H-1,2,4-triazol-1-ylmethyl)-1,3-dioxolan-4-ylmethoxy]phenyl}-2-pyrimidinamine;

4-{4-[2-(2-chloro-4-methylphenyl)-2-(1H-1,2,4-triazol-1-ylmethyl)-1,3-dioxolan-4-ylmethoxy]phenyl}-N-propyl-2-pyrimidinamine;

4-{4-[2-(5-chloro-2-thienyl)-2-(1H-imidazol-2-ylmethyl)-1,3-dioxolan-4-ylmethoxy]phenyl}-N-methyl-2-pyrimidinamine.

EXAMPLE XLIV

Following the procedure of Example XXXI and using equivalent amounts of the appropriate starting materials there are also prepared:

trans-N-[4-{4-[2-(2,4-dichlorophenyl)-2-(1H-imidazol-1-ylmethyl)-1,3-dioxolan-4-ylmethoxy]phenyl}-2-pyrimidinyl]propanamide;

N-[4-{4-[2-(5-chloro-2-thienyl)-2-(1H-imidazol-1-ylmethyl)-1,3-dioxolan-4-ylmethoxy]phenyl}-2-pyrimidinyl]butanamide;

N-[4-{4-[2-(2-thienyl)-2-(1H-1,2,4-triazol-1-ylmethyl)-1,3-dioxolan-4-ylmethoxy]phenyl}-2-pyrimidinyl]acetamide;

N-[4-{4-[2-(2-chloro-4-methylphenyl)-2-(1H-1,2,4-triazol-1ylmethyl)-1,3-dioxolan-4-ylmethoxy]phenyl}-2-pyrimidinyl]propanamide.

EXAMPLE XLV

Following the procedure of Example XXIV and using equivalent amounts of the appropriate starting materials there are also prepared:

trans-4-{4-[2-(2,4-dichlorophenyl)-2-(1H-imidazol-1-ylmethyl)-1,3-dioxolan-4-ylmethoxy]phenyl}-2-pyrimidinol;

4-{4-[4-bromo-2-methylphenyl)-2-(1H-imidazol-1-ylmethyl)-1,3-dioxolan-4-ylmethoxy]phenyl}-2-pyrimidinol;

4-{4-[2-(5-chloro-2-thienyl)-2-(1H-imidazol-1-ylmethyl)-1,3-dioxolan-4-ylmethoxy]phenyl}-2-pyrimidinol;

trans-4-{4-[2-(2,4-dichlorophenyl)-2-(1H-1,2,4-triazol-1-ylmethyl)-1,3-dioxolan-4-ylmethoxy]phenyl}-2-pyrimidinol;

4-{4-[2-(5-bromo-2-thienyl)-2-(1H-1,2,4-triazol-1-ylmethyl)-1,3-dioxolan-4-ylmethoxy]phenyl}-2-pyrimidinol.

EXAMPLE XLVI

Following the procedure of Example XXV and using equivalent amounts of the appropriate starting materials there are also prepared:

trans-4-{4-[2-(2,4-dichlorophenyl)-2-(1H-imidazol-1-ylmethyl)-1,3-dioxolan-4-ylmethoxy]phenyl}-2(1H)-pyrimidinethione;

4-{4-[2-(4-fluorophenyl)-2-(1H-imidazol-1-ylmethyl)-1,3-dioxolan-4-ylmethoxy]phenyl}-2(1H)-pyrimidinethione;

4-{4-[2-(1H-imidazol-1-ylmethyl)-2-(2-thienyl)-1,3-dioxolan-4-ylmethoxy]phenyl}-2(1H)-pyrimidinethione;

cis-4-{4-[2(2,4-dichlorophenyl)-2-(1H-1,2,4-triazol-1-ylmethyl)-1,3-dioxolan-4-ylmethoxy]phenyl}-2(1H)-pyrimidinethione;

4-{4-[2-(5-bromo-2-thienyl)-2-(1H-1,2,4-triazol-1-ylmethyl)-1,3-dioxolan-4-ylmethoxy]phenyl}-2(1H)-pyrimidinethione.

EXAMPLE XLVII

Following the procedure of Example XXVII and using equivalent amounts of the appropriate starting materials there are also prepared:

trans-4-{4-[2-(2,4-dichlororphenyl)-2-(1H-imidazol-1-ylmethyl)-1,3-dioxolan-4-ylmethoxy]phenyl}-2-(methylthio)pyrimidine;

2-(butylthio)-4-{2-(4-fluorophenyl)-2-(1H-imidazol-1-ylmethyl)-1,3-dioxolan-4-ylmethoxy]phenyl}pyrimidine;

4-{4-[2-(1H-imidazol-1-ylmethyl)-2-(2-thienyl)-1,3-dioxolan-4-ylmethoxy]phenyl}-2-(1-methylethylthio)pyrimidine;

cis-4-{4-[2-(2,4-dichlorophenyl)-2-(1H-1,2,4-triazol-1-ylmethyl)-1,3-dioxolan-4-ylmethoxy]phenyl}-2-(ethylthio)pyrimidine;

4-{4-[2-(5-bromo-2-thienyl)-2-(1H-1,2,4-triazol-1-ylmethyl)-1,3-dioxolan-4-ylmethoxy}phenyl}-2-(methylthio)pyrimidine.

EXAMPLE XLVIII

Following the procedure of Example XXXII and using equivalent amounts of the appropriate starting materials there are also prepared:

trans-1-{2-(2,4-dichlorophenyl)-4-[4-(5-isoxazolyl)-phenoxymethyl]-1,3-dioxolan-2-ylmethyl}-1H-imidazole;

1-{4-[4-(5-isoxazolyl)phenoxymethyl]-2-(4-methylphenyl)-1,3-dioxolan-2-ylmethyl}-1H-imidazole;

1-{4-[4-(5-isoxazolyl)phenoxymethyl]-2-(2-thienyl)-1,3-dioxolan-2-ylmethyl}-1H-imidazole;

cis-1-{2-(2,4-dichlorophenyl)-4-[4-(5-isoxazolyl)-phenoxymethyl]-1,3-dioxolan-2-ylmethyl}-1H-1,2,4-triazole;

1-{2-(5-bromo-2-thienyl)-4-[4-(5-isoxazolyl)phenoxymethyl]-1,3-dioxolan-2-ylmethyl}-1H-1,2,4triazole.

EXAMPLE IL

Following procedure of Example XXXIII and using equivalent amounts of the appropriate starting materials there are prepared:

trans-5-{4-[2-(2,4-dichlorophenyl)-2-(1H-imidazol-1-ylmethyl)-1,3-dioxolan-4-ylmethoxy]phenyl}-1-phenyl-1H-pyrazole;

3-{4-[2-(1H-imidazol-1-ylmethyl)-2-(4-methoxyphenyl)-1,3-dioxolan-4-ylmethoxy]phenyl}-1H-pyrazole;

1-[2-(3-chlorophenyl)ethyl]-5-[2-(5-chloro-2-thienyl)-2-(1H-imidazol-1-ylmethyl)-1,3-dioxolan-4-ylmethoxy]phenyl}-1H-pyrazole;

trans-5-{4-[2-(2,4-dichlorophenyl)-2-(1H-1,2,4-triazol-1-ylmethyl)-1,3-dioxolan-4-ylmethoxy]phenyl}-1H-pyrazole-1-ethanol;

1-(3-chlorophenyl)-5-{4-[2-(2-thienyl)-2-(1H-1,2,4-triazol-1-ylmethyl)-1,3-dioxolan-4-ylmethoxy]phenyl}-1H-pyrazole.

EXAMPLE L

Following the procedure of Example XXXIV and using equivalent amounts of the appropriate starting materials are prepared:

trans-4-{4-[2-(2,4-dichlorophenyl)-2-(1H-imidazol-1-ylmethyl)-1,3-dioxolan-4-ylmethoxy]phenyl}-1-methyl-1H-imidazole;

4-{4-[2-(2-chloro-4-methoxyphenyl)-2-(1H-imidazol-1-ylmethyl)-1,3-dioxolan-4-ylmethoxy]phenyl}-1-ethyl-2-(ethylthio)-1H-imidazole;

4-{4-[2-(5-chloro-2-thienyl)-2-(1H-imidazol-1-ylmethyl)-1,3-dioxolan-4-ylmethoxy]phenyl}-2-[3-(2,4-dichlorophenyl)propylthio]-1-ethyl-1H-imidazole;

cis-4{2-(2,4-dichlorophenyl)-2-(1H-1,2,4-triazol-1-ylmethyl)-1,3-dioxolan-4-ylmethoxy]phenyl}-1-methyl-1H-imidazole;

4-{4-[2-(4-bromophenyl)-2-(1H-1,2,4-triazol-1-ylmethyl)-1,3-dioxolan-4-ylmethoxy]phenyl}-2-ethyl-1-(phenylmethyl)-1H-imidazole;

1-ethyl-2-propyl-4-{4-[2-(2-thienyl)-2-(1H-1,2,4-triazol-1-ylmethyl)-1,3-dioxolan-4-ylmethoxy]phenyl}-1H-imidazole;

trans-5-{4-[2-(2,4-dichlorophenyl)-2-(1H-imidazol)-1-ylmethyl)-1,3-dioxolan-4-ylmethoxy]phenyl}-1-(1-methylethyl)-1H-imidazole;

2-(ethylthio)-5-{4-[2-(1H-imidazol-1-ylmethyl)-2-(2-thienyl)-1,3-dioxolan-4-ylmethoxy]phenyl}-1-propyl-1H-imidazole;

5-{4-[2-(4-bromophenyl)-2-(1H-imidazol-1-ylmethyl)-1,3-dioxolan-4-ylmethoxy]phenyl}-2-butyl-1H-imidazole;

5-{4-[2-(5-bromo-2-thienyl)-2-(1H-imidazol)-1-ylmethyl)-1,3-dioxolan-4-ylmethoxy]phenyl}-2-(2-phenylethyl)-1-(phenylmethyl)-1H-imidazole;

trans-2-{4-[2-(2,4-dichlorophenyl)-2-(1H-imidazol-1-ylmethyl)-1,3-dioxolan-4-ylmethoxy]phenyl}-ethyl}-1H-imidazole;

1-butyl-2-{4-[2-(1H-imidazol-1-ylmethyl-2-(2-thienyl)-1,3-dioxolan-4-ylmethoxy]phenyl}-4-(phenylmethyl)-1H-imidazole;

cis-2-{4-[2-(2-chloro-4-methylphenyl)-2-(1H-1,2,4-triazol-1-ylmethyl)-1,3-dioxolan-4-ylmethoxy]phenyl}-1-(2-phenylethyl)-1H-imidazole;

1-butyl-2-{4-[2-(5-chloro-2-thienyl)-2-(1H-1,2,4-triazol-1-ylmethyl)-1,3-dioxolan-4-ylmethoxy]phenyl{-1H-imidazole;

trans-1-{2-(2,4-dichlorophenyl)-4-[4(2-methyl-4-thiazolyl)-phenoxymethyl]-1,3-dioxolan-2-ylmethyl}-1H-imidazole;

1-[2-(4-methylphenyl)-4-{[2-(3-methylpentyl)-5-thiazolyl]-phenoxymethyl}-1,3-dioxolan-2-ylmethyl]-1H-imidazole;

[4-{4-[4-(phenylmethyl)-2-thiazolyl]phenoxymethyl}-2-(2-thienyl)-1,3-dioxolan-2-ylmethyl]-1H-1,2,4-triazole; p0 1-{2-(4-bromophenyl)-4-[4-(2-propyl-4-thiazolyl)phenoxymethyl]-1,3-dioxolan-2-ylmethyl}-1H-1,2,4-triazole;

1-[2-(5-bromo-2-thienyl)-4-{4-[2-(phenylmethyl)-4-oxazolyl]-phenoxymethyl}-1,3dioxolan-2-ylmethyl]-1H-imidazole;

1-{4-[4-(2-ethyl-5-oxazolyl)phenoxymethyl]-2-(2-methylphenyl)-1,3-dioxolan-2-ylmethyl}-1H-1,2,4-triazole;

1-{4-(2-oxazolyl)phenoxymethyl]-2-(2-thienyl)-1,3-dioxolan-2-ylmethyl}-1H-1,2,4triazole;

trans-2-{4-[2-(2,4-dichlorophenyl)-2-(1H-imidazol-1-ylmethyl)-1,3-dioxolan-4-ylmethoxy]phenyl{-1,3,4-oxadiazole;

2-{4-[2-(1H-imidazol-1-ylmethyl)-2-(3-methoxyphenyl)-1,3-dioxolan-4-ylmethoxy]phenyl}-5-methyl-1,3,4-oxadiazole;

5-butyl-2-{4-[2-(5-chloro-2-thienyl)-2-(1H-imidazol-1-ylmethyl)-1,3-dioxolan-4-ylmethoxy]phenyl}-1,3,4-oxadiazole;

trans-2-{4-[2-(2,4-dichlorophenyl)-2-(1H-1,2,4-triazol-1-ylmethyl)-1,3-dioxolan-4-ylmethoxy]phenyl}-5-methyl-1,3,4-oxadiazole;

2-{4-[2-(2-methylphenyl)-2-(1H-1,2,4-triazol-1-ylmethyl)-1,3-dioxolan-4-ylmethoxy]phenyl}-1,3,4-oxadiazole;

5-pentyl-2-{4-[2-(2-thienyl)-2-(1H-1,2,4-triazol-1-ylmethyl)-1,3-dioxolan-4-ylmethoxy]phenyl}-1,3,4-oxadiazole.

What is claimed is:

1. A chemical compound selectd from the group consisting of an azole derivative having the formula:

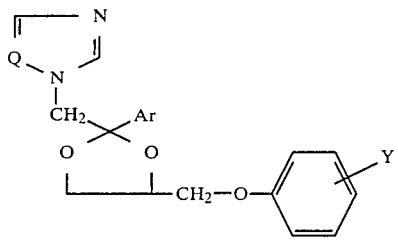

and the pharmaceutically acceptable acid addition salts and stereochemically isomeric forms thereof, wherein:

Q is a member selected from the group consisting of CH and N;

Ar is a member selected from the group consisting of thienyl, halothienyl, phenyl and substituted phenyl, said substituted phenyl having from 1 to 3 substituents each independently selected from the group consisting of haol, lower alkyl and lower alkyloxy; and the radical Y is a pyrimidin-4-yl radical of the formula

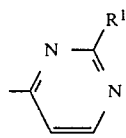 (a)

wherein R¹ is a member selected from the group consisting of hydrogen, lower alkyl, lower alkenyl, lower alkynyl, lower alkyloxy, lower alkenyloxy, lower alkynyloxy, lower alkyloxy-lower alkyloxy, aryllower alkyloxy, lower alkylthio, aryllower alkylthio, hydroxy, mercapto, amino, mono- and di-lower alkylamino, cycloalkylamino, lower alkylcarbonylamino, arylcarbonylamino, arylamino, aryl lower alkylamino and aryl;

wherein said aryl as used in the foregoing definitions is selected from the group consisting of phenyl and substituted phenyl, said substituted phenyl having from 1 to 3 substituents each independently selected from the group consisting of halo, lower alkyl, lower alkyloxy and trifluoromethyl.

2. A chemical compound selectd from the group consisting of cis-4-{4-[2-(2,4-dichlorophenyl)-2-(1H-imidazol-1-ylmethyl)-1,3-dioxolan-4-ylmethoxy]-phenyl}pyrimidine and the pharmaceutically accepted acid addition salts and stereochemically isomeric forms thereof.

3. A chemical compound selected from the group consisting of cis-4-{4-[2-(2,4-dichlorophenyl)-2-(1H-imidazol-1-ylmethyl)-1,3-dioxolan-4-ylmethoxy]-phenyl}-N-methyl-2-pyrimidinamine and the pharmaceutically acceptable acid addition salts and stereochemically isomeric forms thereof.

4. A composition for combating a microorganism selected from the group consisting of fungus and bacterium comprising an inert carrier material and as an active ingredient an effective antifungal or antibacterial amount of a compound selected from the group consisting of an azole derivative having the formula

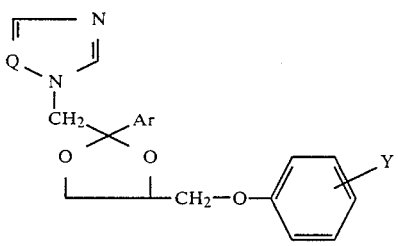

and the pharmaceutically acceptable acid addition salts and stereochemically isomeric forms thereof, wherein:

Q is a member selected from the group consisting of CH and N;

Ar is a member selected from the group consisting of thienyl, halothienyl, phenyl and sustituted phenyl, said substituted phenyl having from 1 to 3 substituents each independently selected from the group consisting of halo, lower alkyl and lower alkyloxy; and the radical Y is a pyrimidin-4-yl radical of the formula

 (a)

wherein R¹ is a member selected from the group consisting of hydrogen, lower alkyl, lower alkenyl, lower alkynyl, lower alkyloxy, lower alkenyloxy, lower alkynyloxy, lower alkyloxy-lower alkyloxy, aryllower alkyloxy, lower alkylthio, aryllower alkylthio, hydroxy, mercapto, amino, mono- and di-lower alkylamino, cycloalkylamino, lower alkylcarbonylamino, arylcarbonylamino, arylamino, aryl lower alkylamino and aryl;

wherein said aryl as used in the foregoing definitions is selected from the group consisting of phenyl and substituted phenyl, said substituted phenyl having from 1 to 3 substituents each independently selected from the group consisting of halo, lower alkyl, lower alkyloxy and trifluoromethyl.

* * * * *

UNITED STATES PATENT AND TRADEMARK OFFICE
CERTIFICATE OF CORRECTION

PATENT NO. : 4,533,550

DATED : August 6, 1985

INVENTOR(S) : Heeres, et al.

It is certified that error appears in the above—identified patent and that said Letters Patent is hereby corrected as shown below:

Claim 1, line 9 delete "haol" insert -- halo --.

Claim 2, line 2 delete "cis" insert -- cis --.

Claim 2, line 4 delete "accepted" insert -- acceptable --.

Signed and Sealed this

Tenth Day of June 1986

[SEAL]

Attest:

DONALD J. QUIGG

*Attesting Officer*   *Commissioner of Patents and Trademarks*